US006312899B1

(12) United States Patent
Crabtree et al.

(10) Patent No.: US 6,312,899 B1
(45) Date of Patent: *Nov. 6, 2001

(54) NF-AT POLYPEPTIDES AND POLYNUCLEOTIDES

(75) Inventors: Gerald R. Crabtree, Woodside; Jeffrey P. Northrop, Campbell; Steffan N. Ho, Menlo Park, all of CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/338,128

(22) Filed: Jun. 22, 1999

Related U.S. Application Data

(63) Continuation of application No. 08/260,174, filed on Jun. 13, 1994, now Pat. No. 6,197,925, which is a continuation-in-part of application No. 08/124,981, filed on Sep. 20, 1993, now Pat. No. 5,837,840.

(51) Int. Cl.$^7$ .............................. C12Q 1/68; C07H 21/04
(52) U.S. Cl. ...................... 435/6; 536/24.31; 536/24.33
(58) Field of Search .............................. 435/6; 536/23.1, 536/23.5, 24.3, 24.31, 24.33

(56) References Cited

U.S. PATENT DOCUMENTS

| 5,656,452 | 8/1997 | Rao et al. | 435/69.1 |
| 5,837,840 | * 11/1998 | Crabtree et al. | 536/23.4 |

FOREIGN PATENT DOCUMENTS

| WO 93/04203 | 3/1993 | (WO) . |
| WO 94/15964 | 7/1994 | (WO) . |
| WO 95/02053 | 1/1995 | (WO) . |

OTHER PUBLICATIONS

Clipstone, N. and Crabtree, G., "Calcineurin is a key signaling enzyme in T lymphocyte activation and the target of the immunosuppressive drugs cyclosporin A and FK506", *Ann. N. Y. Acad. Sci.*, 696: 20–30 (1993).
Clipstone, N. and Crabtree, G., "Identification of calcineurin as a key signaling enzyme in T–lymphocyte activation" *Nature*, 357(6380): 695–697.
Crabtree, G. and Clipstone, N., "Signal transmission between the plasma membrane and nucleus of T. lymphocyte", *Ann. Rev. Biochem.*, 63: 1045–1083 (1994).
Ho, S. et al., Cloning and characterization of NF–AT$_c$ and NF–AT$_p$ : the cytoplasmic components of NF–AT, *Adv.Exp Med. Biol.* 365:167 (1994).
Jain, J. et al., "The T cell transcription factor NF–AT$_p$ is a subtrate for calcineurin with Fos and Jun", *Nature*, 365(6444): 352–355 (1993).
Jain, J. et al., "Analysis of the preexisting and nuclear forms of nuclear factor of activated T cells", *J. Immunol.*, 151(2): 837–848 (1993).

Jain, J. et al., "Nuclear Factor of activated T cells contains Fos and Jun". *Nature*, 356(6372): 801–804 (1992).
McCaffrey, P. et al., "NF–AT$_p$, a T lymphocyte DNA–binding protein that is a target for calcineurin and immunosuppressive drugs", *J. Biol. Chem.*, 268(5): 3747–3752 (1993).
McCaffrey, P. et al., "Isolation of the cyclosporin–sensitive T cell transcription factor NF–AT$_p$", *Science*, 262: 750–754 (1993).
Northrop, J. et al., "NF–AT components define a family of transcription factors targeted in T–cell activation", *Nature* 369: 497–502 (1994).
Northrop et al. "Characterization of the nuclear and cytoplasmic components of the lymnphoid–specific nuclear factor of activated T Cells (NF–AT) complex" *J. Biol. Chem.* 268:2917 (1993).
Verweij, C. et al., "Cell type and activation requirements for NFAT–1 (nuclear factor of activated T–cells) transcriptional activity determined by a new method using transgenic mice to assay transcriptional activity of an individual nuclear factor", *J. Biol. Chem.*, 265 ( 26): 15788–15795 (1990).
Rao, A., "NF–AT$_p$: a transcription factor required for the co–ordinatre induction of several cytokine genes", *Immunology Today*, 15(6): 274–281 (1994).
Bierer, B. et al., "Two distinct signal transmision pathways in T lymphocytes are inhibited by complexes formed between an immunophilin and either FK506 or rapamycin", *Proc. Nat. Acad. Sci. USA*, 87: 9231–9235 (1990).
Flanagan, W. et al., "Nuclear association of a T–cell transcription factor blocked by FK–506 and cyclosporin A", *Nature*, 352: 803–807 (1991).
Israel, A., "NF–AT comes under control", *Nature*, 369: 443–444 (1994).

(List continued on next page.)

Primary Examiner—Robert A. Schwartzman
(74) Attorney, Agent, or Firm—Matthew P. Vincent; Ropes & Gray, LLP

(57) ABSTRACT

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

27 Claims, 18 Drawing Sheets

OTHER PUBLICATIONS

Crabtree G. "Pathways of T lymphocyte activation" Abstract of NIH Grant No. R01CA39612 (1988).

Crabtree G. "Pathways of T lymphocyte activation" Abstract of NIH Grant No. R01CA39612 (1991).

Shaw et al. "Identification of putative regulator of early T cell activation genes" *Science* 241:202 (1988).

Crabtree G. "Contingent genetic regulatory events in T lynphocyte activation" *Science* 243:355 (1989).

Emmel et al. "Cyclosporin A specifically inhibits function of nuclear proteins involved in T cell activation" Science 246:1617 (1989).

Schmidt et al. "Inducible nuclear factor binding to the kB element of the human immunodeficiency virus enhancer in T cells can be blocked by cyclosporin a in a signal–dependent manner" *J. Virol.* 64:4037 (1990).

Mattila et al. "the actions of cyclosporin A and FK506 suggest a novel step in the activation of T lymphocytes" *EMBO J* 9:4425 (1990).

Banerji et al. "The immunosuppressant FK–506 specifically inhibits mitogen induced activation of the interleukin–2 promoter and the isolated enhancer elements NFIL–2A and NF–AT1" *Mol. Cell. Biol.* 11: 4074 (1991).

Riegel et al. "Nuclear events after activation of CD4+CD8+ thymoytes" *J. Immunol.* 144:3611 (1990).

* cited by examiner

```
                                  .         .         .         .         .         .         .         .         .
                                 10        30        50        70        90
       gaattccgcagggcgcggggacccggggcgcaggcctcggagccaggtcctagggccgccaccgccgggcccgccacgccgcacacgcccc
                                 110       130       150       170       190
                                  .         .         .         .         .         .         .         .         .
       tcgatgactttcctccggggcgcgctgagccgggcgagggctgtcttccggagaccgaccccagcgcggggcggccacttctcctgtg
                                 210       230       250       270       290
                                  .         .         .         .         .         .         .         .         .
       cctccgcccgctgctccactcccgccgccgatgccaagccaccagtttccagtcccttccaagtttccacttggcctgcctgcggtct        21
                                 310       330       350       370       390
                                                     M  P  S  T  S  F  P  V  P  S  K  F  P  L  G  P  A  A  V  F
                                  .         .         .         .         .         .         .         .         .
       tcgggaggagaaactttgggcgcggcgcgccgcggcaccatgaagtcagcggaggaagaacactatggctatgcatcctccaagtcagccc          54
                                 410       430       450       470       490
        G  R  E  T  L  G  P  A  P  R  A  G  T  M  K  S  A  E  E  E  H  Y  G  Y  A  S  S  N  V  S  P
                                  .         .         .         .         .         .         .         .         .
       cgccctgccgctcccacggcgcactccacctgccgccaacccttcagacctccacacgggcatcatcccgccggatcaccctcg                87
                                 510       530       550       570       590
        A  L  P  L  P  T  A  H  S  T  L  P  A  P  C  H  N  L  Q  T  S  T  P  G  I  I  P  P  A  D  H  P  S
                                  .         .         .         .         .         .         .         .         .
       gggtacggagcagtttgacggtgggcccggcgcgggctactcctcctccggccacaccaggcctgatggggcctgcctggagagtcctcgcatcg       121
        G  Y  G  A  A  L  D  G  G  P  A  G  Y  F  L  S  S  G  H  T  R  P  D  G  A  P  A  L  E  S  P  R  I  E
```

FIG. 1A

```
                 agataacctgtgcttggcctgtaccacaacaataaccagttttccacgatgtggaggtggaagacgtctcctagtccaaacgtcccctccac
122              I  T  S  C  L  G  L  Y  H  N  N  N  Q  F  F  H  D  V  E  V  E  D  V  L  P  S  S  K  R  S  P  S  T    154
                 610          630          650          670          690
                                      710                      750                      790 ggccacgctgagtctgccagcctgctgccccctctgtgctgagccgcagccctgagccccctgagccctgcaactcagaggcctcc
155              A  T  L  S  L  P  S  L  E  A  Y  R  D  P  S  C  L  S  P  A  S  S  L  S  R  S  C  N  S  E  A  S    187
                                      810                      850                      890
                                                   830                      870 tcctacgagtccaactactcgtacccgtacgcgtccccagacgtcgccatgcagtcgcctgtgtctcccagacccgaggaggct
188              S  Y  E  S  N  Y  S  Y  P  Y  A  S  P  Q  T  S  P  W  Q  S  P  C  V  S  P  K  T  T  D  P  E  E  G  F    221
                                      910                      950                      990
                                                   930                      970 ttccccgcggctgggggcctgcacactgctgctgggttcccgcagcactccccctcgctgggcagtcactgaggagagctggctgggtgc
222              P  R  G  L  G  A  C  T  L  L  G  S  P  Q  H  S  P  S  T  S  P  R  A  S  V  T  E  E  S  W  L  G  A    254
                                      1010                     1050                     1090
                                                   1030                     1070 ccgctcctccagacccgcgcctccttgcaacaagaggaagtacagcctcaacggccgccagccgccactgccccacgcgctcccg
255              R  S  S  R  P  A  S  P  C  N  K  R  K  Y  S  L  N  G  R  Q  P  P  Y  S  P  H  H  S  P  T  P  S  P    287
                                      1110                     1150                     1190
                                                   1130                     1170 cacggctccccgcgggtcagcgtgacggacgactcgtggttgggcaacaccacccagtacaccacccagtataccagctggcagctgacca
288              H  G  S  P  R  V  S  V  T  D  D  S  W  L  G  N  T  T  Q  Y  T  S  A  I  V  A  A  I  N  A  L  T  T    321
```

FIG. 1B

```
            1210            1230            1250            1270            1290
      ccgacagcagcctggagacctggggagatggcgtccctgtcaagtcccgcaagaccaccctggacagcagccctcagtggcgctcaagtggagcccgtcgg    354
322   D  S  S  L  D  L  G  D  D  G  V  P  P  V  K  S  R  K  T  T  L  E  Q  P  P  S  V  A  L  K  V  E  P  V  G
                        1310            1330            1350            1370            1390 ggaggacctgggcagccccccgccccggcgacttcgcggccgaagacttcgccccggccgactttgctgctccggccctcctctttccagcacatcaggaagggcggcttctgcgaccagtacctg    387
355   E  D  L  G  S  P  P  P  P  A  D  F  A  P  E  D  Y  S  S  F  Q  H  I  R  K  G  G  F  C  D  Q  Y  L
                        1410            1430            1450            1470            1490 gcggtgccgcagcacccctaccagtgggcaaagcccaagcccaagtgggaagtgccaagcccaagcccaagcctctcccgtcccctgcccgcctgactggcagctgcctgcagctgcctgccgt    421
388   A  V  P  Q  H  P  Y  Q  W  A  K  P  K  P  L  S  P  T  S  Y  M  S  P  T  L  P  A  L  D  W  Q  L  P  S
                        1510            1530            1550            1570            1590 cccactcaggccgtatgagcttcgagttgaggttgcagccaagtcccaccaccaccgagcccaagtcccaccaccgagacgaggagcagcggggggccgtgaaggcgtc    454
422   H  S  G  P  Y  E  L  R  I  E  V  Q  P  K  S  H  H  R  A  H  Y  E  T  E  G  S  R  G  A  V  K  A  S
                        1610            1630            1650            1670            1690 ggccggagagacccatcgtgcagctgcatggctactggagaatgagcgctgcagttttcattgggacggcggcgaccgcctgctgcgc    487
455   A  G  G  H  P  I  V  Q  L  H  G  Y  L  E  N  E  P  L  M  L  Q  L  F  I  G  T  A  D  D  R  L  L  R
                        1710            1730            1750            1770            1790 ccgcaccgcctttctaccaggtgcaccgcatcacagggaagaccgtgtccaccaccagccacgaggctatcctctccaacaccaagtcctggagatcccac    521
488   P  H  A  F  Y  Q  V  H  R  I  T  G  K  T  V  S  T  T  S  H  E  A  I  L  S  N  T  K  V  L  E  I  P  L
```

FIG. 1C

```
     tcctgccggagaacagcatgcgagccgtcattgactgtgccgaatcctgaaactcgacattgaacttcggaaggagaacggacatcgg
522  L  P  E  N  S  M  R  A  V  I  D  C  A  G  I  L  K  L  R  N  S  D  I  E  L  R  K  G  E  T  D  I  G    554
     1810             1830             1850             1870             1890 gaggaagaacacacgggtgtacggctggttccggcttcacgtcccgcaacccagcggccgcacgtcctctgcaggtggcctccaacccatcgaatgc
555  R  K  N  T  R  V  R  L  V  F  R  V  H  V  P  Q  P  S  G  R  T  L  S  L  Q  V  A  S  N  P  I  E  C    587
     1910             1930             1950             1970             1990 tcccagcgctcagctcaggagctgcctctggtggagaagcagagcacggacagctatccggttgtgggcgggaagaagatgtcctgtctgccacaact
588  S  Q  R  S  A  Q  E  L  P  L  V  E  K  Q  S  T  D  S  Y  P  V  V  G  G  K  K  M  V  L  S  G  H  N  F    621
     2010             2030             2050             2070             2090 tcctgcaggactccaaggtcatttttcgtggagaaagccccagatggccaccatgtctgggagatggaagcgaaaactgacgggaccctgtcaagccgaa
622  L  Q  D  S  K  V  I  F  V  E  K  A  P  D  G  H  H  V  W  E  M  E  A  K  T  D  R  D  L  C  K  P  N    654
     2110             2130             2150             2170             2190 ttctctggtggttgagatcccgccattcgaatcagaggataaccagcccgttcacgtcagtttctacgtctgcaacgggaagagaagcgaagccag
655  S  L  V  E  I  P  P  F  R  N  Q  R  I  T  S  P  V  H  V  S  F  Y  V  C  N  G  K  R  K  R  S  Q    687
     2210             2230             2250             2270             2290 taccagcgtttcacctacttcccgccaacgcctaagccgtgaacatgagccgtggggtgcttttctaaagacgcagaa
688  Y  Q  R  F  T  Y  L  P  A  N  G  N  A  I  F  L  T  V  S  R  E  H  E  R  V  G  C  F  F
     2310             2330             2350             2370             2390
```

FIG. 1D

```
         2410            2430            2450            2470            2490
          .               .               .               .               .
acgacgtcgccgtaaagcagcggcgtggcgtgttgcacatttaactgtgtgatgtcccgttagtgagaccgagccatcgatgccctgaaaaggaaggaaaag
          .               .               .               .               .
         2510            2530            2550            2570            2590
ggaagcttcgatgcatttcctgatccctgttggggtgggggcggggggttgcatactcagatagtcacggttattttgcttcttgcgaatgtataa
          .               .               .               .               .
         2610            2630            2650            2670            2690
cagccaaggggaaaacatggctctttctgctccaaaaaactgaggggtcctggtgtgcatttgcaccctaaagctgcttacggtgaaaaggcaaataggt
          .               .               .               .               .
         2710            2730            2750
atagctattttgcaggcacctttaggaataaactttgcttttaaaaaaaaa
          .               .               .
```

```
              418
DMDORSAL   TKNVRKKPYVKITE-QPAGKALRFRYECEGRSAGSIPGVNSTPENKT
C-REL      MASGLYNPYIEIIE-QPRQRGMRFRYKCEGRSAGSIPQEHSTDNNRT
NFKB p50   IPLSTDGPYLQILE-QPKQRGFRFRYVCEGPSHGGLPGASSEKNKKS
NFKB p65   EPAQASGPYVEIIE-QPKQRGMRFRYKCEGRSAGSIPGERSTDTTKT
NFATc      QLPSHSGPYELRIEVQPKSH-HRAHYETEG-SRGAVKASAGG----
NFATp      PLSNQSGSYELRIEVQPKPH-HRAHYETEG-SRGAVKAPTGG----
                                       *              *       457

458                                           505
DMDORSAL   YPTIEIVGYKGRAVVVSCVTKDTPYRP-HPHNLVGKEGCK-KGVCTLEI
C-REL      YPSINIMNYYGRGKVRITLVTKNDPYKP-HPHDLVGKD-CR-DGYYEAEF
NFKB p50   YPQVKICNYVGPAKVIVQLVTNGKNIHL-HAHSLVGKH-CE-DGVCTVTA
NFKB p65   HPTIKINGYTGPGTVRISLVTKDPPHRP-HPHELVGKD-CR-DGYYEADL
NFATc      HPIVQLHGYLENEPLMLQLFIGTADDRLLRPHAFYQV--HRITGKTVSTT
NFATp      HPVVQLHGYMENKPLGLQIFIGTADERILKPHAFYQV--HRITGKTVTTT
                                       *              *

506                                           542
DMDORSAL   NSE-TMRAVFSNLGIQCVKKKDIEAALKAR-EEIRVDPFKTGFSHRF---
C-REL      GNE-RRPLFFQNLGIRCVKKKEVKEAIITRIKAG-INPFN---------
NFKB p50   GPK-DMVGFANLGILHVT-KKKVFETLEARMTEACIRGYNPGLLVHSDL
NFKB p65   CPDRDSIHSFQNLGIQCVKKRDLEQAIS-QRIQTNNPFH---------
NFATc      SHE-AILSNTKVLEIPLLPENSMRAVIDCAGILKLRNS---------
NFATp      SYE-KIVGNTKVLEIPLEPKNNMRATIDCAGILKLRNA---------
                                       *              *
```

```
DMDORSAL   -------------------------------------QPSSIDLNSVRLCFQVFMESEQK
C-REL      ---------VPEKQLNDIE-------------------------DCDLNVRLCFQVFL-PDEH
NFKB p50   AYLQAEGGGDRQLTDREKEIIRQAAVQQTKEMDLSVVRLMFTAFL-PDST
NFKB p65   ------------VPIEE---------------------QRGDYDLNAVRLCFQVTV-RDPA
NFATc      ------------DIE-----------------------LRKGETDIGRKNTRVRLVFRVHV-PQPS
NFATp      ------------DIE-----------------------LRKGETDIGRKNTRVRLVFRVHV-PEPS
                        543                                              572
                        *                                                *

DMDORSAL   GRFTSPLPPVVSEPIFDKKA---MSDLVICRL-CSCSATVFGNTQIILLCE
C-REL      GNLTTALPPVVSNPIYDNRAPNTAELRICRV-NKNCGSVRGGDEIFLLCD
NFKB p50   GSFTRRLEPVVSDAIYDSKAPNASNLKIVRM-DRTAGCVTGGEEIYLLCD
NFKB p65   GRPLL-LTPVLSHPIFDNRAPNTAELKICRV-NRNSGSCLGGDEIFLLCD
NFATc      GRTLS-L-QVASNPI-----ECSQRSAQELPLVEKQSTDSYPVVGGKKMVLS-G
NFATp      GRIVS-L-QAASNPI-----ECSQRSAHELPMVERQDMDSCLVYGGQQMILT-G
                573                                              618
                *                                                *

DMDORSAL   KVAKEDISVRFEEKNGQ--SVWEAFGDFQHTDVHKQTAITFKTPRYHTLD
C-REL      KVQKDDIEVRFFEEKNGQ--NDWEAKGIFSQADVHRQVAIVFKTPPYCK-A
NFKB p50   KVQKDDIQIRFYEEENG--GVWEGFGDFSPTDVHRQFAIVFKTPKYKDVN
NFKB p65   KVQKEDIEVYFTG-----PGWEARGSFSQADVHRQVAIVFRTPPYADPS
NFATc      HNFLQDSKVIFVEKAPDGHHVWEMEAKT-DRDLCKPNSLVVEIPPFRNQR
NFATp      QNFTAESKVVFMEKTTDGQQIWEMEATV-DKDKSQPNMLFVEIPEYRNKH
           *                                                667
                                                            619
```

FIG. 4B

SEQUENCE LISTING

<160> NUMBER OF SEQ ID NOS: 52

<210> SEQ ID NO 1
<211> LENGTH: 36
<212> TYPE: DNA
<213> ORGANISM: Homo sapiens

<400> SEQUENCE: 1
ttcctccggg gcgcgcggcg tgagcccggg gcgagg                36

<210> SEQ ID NO 2
<211> LENGTH: 42
<212> TYPE: DNA
<213> ORGANISM: Homo sapiens

<400> SEQUENCE: 2
cagcgcgggg cggccacttc tcctgtgcct ccgcccgctg ct         42

<210> SEQ ID NO 3
<211> LENGTH: 42
<212> TYPE: DNA
<213> ORGANISM: Homo sapiens

<400> SEQUENCE: 3
gccgcgcgga tgccaagcac cagctttcca gtcccttcca ag        42

<210> SEQ ID NO 4
<211> LENGTH: 42
<212> TYPE: DNA
<213> ORGANISM: Homo sapiens

<400> SEQUENCE: 4
ccaacgtcag ccccgccctg ccgctcccca cggcgcactc ca        42

<210> SEQ ID NO 5
<211> LENGTH: 36
<212> TYPE: DNA
<213> ORGANISM: Homo sapiens

<400> SEQUENCE: 5
ttcagacctc cacaccgggc atcatcccgc cggcgg        36

<210> SEQ ID NO 6
<211> LENGTH: 42
<212> TYPE: DNA
<213> ORGANISM: Homo sapiens

<400> SEQUENCE: 6
gccacaccag gcctgatggg gccctgccc tggagagtcc tc        42

<210> SEQ ID NO 7
<211> LENGTH: 42
<212> TYPE: DNA
<213> ORGANISM: Homo sapiens

<400> SEQUENCE: 7
agtctgccca gcctggaggc ctacagagac ccctcgtgcc tg        42

<210> SEQ ID NO 8
<211> LENGTH: 39
<212> TYPE: DNA
<213> ORGANISM: Homo sapiens

<400> SEQUENCE: 8
gtgtctccca agaccacgga ccccgaggag ggctttccc        39

<210> SEQ ID NO 9
<211> LENGTH: 42
<212> TYPE: DNA
<213> ORGANISM: Homo sapiens

<400> SEQUENCE: 9
agctggctgg gtgcccgctc ctccagaccc gcgtcccctt gc        42

<210> SEQ ID NO 10
<211> LENGTH: 42
<212> TYPE: DNA
<213> ORGANISM: Homo sapiens

<400> SEQUENCE: 10
tacagcctca acggccggca gccgccctac tcaccccacc ac        42

<210> SEQ ID NO 11
<211> LENGTH: 42
<212> TYPE: DNA
<213> ORGANISM: Homo sapiens

<400> SEQUENCE: 11
gaccaccgac agcagcctgg acctgggaga tggcgtccct gt         42

<210> SEQ ID NO 12
<211> LENGTH: 42
<212> TYPE: DNA
<213> ORGANISM: Homo sapiens

<400> SEQUENCE: 12
cctgggcagc ccccgcccc cggccgactt cgcgcccgaa ga           42

<210> SEQ ID NO 13
<211> LENGTH: 42
<212> TYPE: DNA
<213> ORGANISM: Homo sapiens

<400> SEQUENCE: 13
gctcccctac cagtggcgaa gcccaagccc ctgtcccta cg          42

<210> SEQ ID NO 14
<211> LENGTH: 42
<212> TYPE: DNA
<213> ORGANISM: Homo sapiens

<400> SEQUENCE: 14
cttcggattg aggtgcagcc caagtcccac caccgagccc ac         42

<210> SEQ ID NO 15
<211> LENGTH: 42
<212> TYPE: DNA
<213> ORGANISM: Homo sapiens

<400> SEQUENCE: 15
catggctact tggagaatga gccgctgatg ctgcagcttt tc          42

<210> SEQ ID NO 16
<211> LENGTH: 42
<212> TYPE: DNA
<213> ORGANISM: Homo sapiens

<400> SEQUENCE: 16
aagaccgtgt ccaccaccag ccacgaggct atcctctcca ac          42

<210> SEQ ID NO 17
<211> LENGTH: 42
<212> TYPE: DNA
<213> ORGANISM: Homo sapiens

<400> SEQUENCE: 17
tcagctcagg agctgcctct ggtggagaag cagagcacgg ac          42

<210> SEQ ID NO 18
<211> LENGTH: 40
<212> TYPE: DNA
<213> ORGANISM: Homo sapiens

<400> SEQUENCE: 18
aacgccatct ttctaaccgt aagccgtgaa catgagcgcg              40

<210> SEQ ID NO 19
<211> LENGTH: 38
<212> TYPE: DNA
<213> ORGANISM: Homo sapiens

<400> SEQUENCE: 19
agaaacgacg tcgccgtaaa gcagcgtggc gtgtggca                               38

<210> SEQ ID NO 20
<211> LENGTH: 41
<212> TYPE: DNA
<213> ORGANISM: Homo sapiens

<400> SEQUENCE: 20
gcatactcag atagtcacgg ttattttgct tcttgcgaat g                           41

<210> SEQ ID NO 21
<211> LENGTH: 36
<212> TYPE: DNA
<213> ORGANISM: Homo sapiens

<400> SEQUENCE: 21
agggcgcggg caccggggcg cgggcagggc tcggag                                 36

<210> SEQ ID NO 22
<211> LENGTH: 36
<212> TYPE: DNA
<213> ORGANISM: Homo sapiens

<400> SEQUENCE: 22
gcaagaagca aaataaccgt gactatctga gtatgc                                 36

<210> SEQ ID NO 23
<211> LENGTH: 13
<212> TYPE: PRT
<213> ORGANISM: Homo sapiens

<400> SEQUENCE: 23

Ser Pro Arg Ala Ser Val Thr Glu Glu Ser Trp Leu Gly
 1               5                  10

<210> SEQ ID NO 24
<211> LENGTH: 13
<212> TYPE: PRT
<213> ORGANISM: Homo sapiens

<400> SEQUENCE: 24

Ser Pro Arg Val Ser Val Thr Asp Asp Ser Trp Leu Gly
 1               5                  10

<210> SEQ ID NO 25
<211> LENGTH: 16
<212> TYPE: PRT
<213> ORGANISM: Homo sapiens

<400> SEQUENCE: 25

Asn Ala Ile Phe Leu Thr Val Ser Arg Glu His Glu Arg Val Gly Cys
 1               5                  10                  15

<210> SEQ ID NO 26
<211> LENGTH: 18
<212> TYPE: PRT
<213> ORGANISM: Homo sapiens

<400> SEQUENCE: 26

Leu His Gly Tyr Leu Glu Asn Glu Pro Leu Met Leu Gln Leu Phe Ile
 1               5                  10                  15
Gly Thr

<210> SEQ ID NO 27
<211> LENGTH: 16
<212> TYPE: PRT
<213> ORGANISM: Homo sapiens

<400> SEQUENCE: 27

Pro Ser Thr Ser Pro Arg Ala Ser Val Thr Glu Glu Ser Trp Leu Gly
 1               5                  10                  15

<210> SEQ ID NO 28
<211> LENGTH: 19
<212> TYPE: PRT
<213> ORGANISM: Homo sapiens

<400> SEQUENCE: 28

Gly Pro Ala Pro Arg Ala Gly Gly Thr Met Lys Ser Ala Glu Glu Glu
 1               5                  10                  15
His Tyr Gly

<210> SEQ ID NO 29
<211> LENGTH: 10
<212> TYPE: PRT
<213> ORGANISM: Homo sapiens

<400> SEQUENCE: 29

Ala Ser Ala Gly Gly His Pro Ile Val Gln
 1               5                  10

<210> SEQ ID NO 30
<211> LENGTH: 10
<212> TYPE: PRT
<213> ORGANISM: Homo sapiens

<400> SEQUENCE: 30

Asn Thr Arg Val Arg Leu Val Phe Arg Val
 1               5                  10

<210> SEQ ID NO 31
<211> LENGTH: 22
<212> TYPE: PRT
<213> ORGANISM: Homo sapiens

<400> SEQUENCE: 31

Ala Lys Thr Asp Arg Asp Leu Cys Lys Pro Asn Ser Leu Val Val Glu
 1               5                  10                  15
Ile Pro Pro Phe Arg Asn
                 20

<210> SEQ ID NO 32
<211> LENGTH: 18
<212> TYPE: PRT
<213> ORGANISM: Homo sapiens

<400> SEQUENCE: 32

Glu Val Gln Pro Lys Ser His His Arg Ala His Tyr Glu Thr Glu Gly
 1               5                  10                  15

-continued

Ser Arg

<210> SEQ ID NO 33
<211> LENGTH: 15
<212> TYPE: PRT
<213> ORGANISM: Homo sapiens

<400> SEQUENCE: 33

Ser Pro Arg Val Ser Val Thr Asp Asp Ser Trp Leu Gly Asn Thr
 1               5                  10                  15

<210> SEQ ID NO 34
<211> LENGTH: 16
<212> TYPE: PRT
<213> ORGANISM: Homo sapiens

<400> SEQUENCE: 34

Ser His His Arg Ala His Tyr Glu Thr Glu Gly Ser Arg Gly Ala Val
 1               5                  10                  15

<210> SEQ ID NO 35
<211> LENGTH: 17
<212> TYPE: PRT
<213> ORGANISM: Homo sapiens

<400> SEQUENCE: 35

Leu Arg Asn Ser Asp Ile Glu Leu Arg Lys Gly Glu Thr Asp Ile Gly
 1               5                  10                  15

Arg

<210> SEQ ID NO 36
<211> LENGTH: 13
<212> TYPE: PRT
<213> ORGANISM: Homo sapiens

<400> SEQUENCE: 36

Thr Leu Ser Leu Gln Val Ala Ser Asn Pro Ile Glu Cys
 1               5                  10

<210> SEQ ID NO 37
<211> LENGTH: 13
<212> TYPE: PRT
<213> ORGANISM: Homo sapiens

<400> SEQUENCE: 37

Val Lys Ala Ser Ala Gly Gly His Pro Ile Val Gln Leu
 1               5                  10

<210> SEQ ID NO 38
<211> LENGTH: 716
<212> TYPE: PRT
<213> ORGANISM: Homo sapiens

<400> SEQUENCE: 38

Met Pro Ser Thr Ser Phe Pro Val Pro Ser Lys Phe Pro Leu Gly Pro
 1               5                  10                  15

Ala Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
                35                  40                  45

Ser Ser Asn Val Ser Pro Ala Leu Pro Leu Pro Thr Ala His Ser Thr
        50                  55                  60

-continued

```
Leu Pro Ala Pro Cys His Asn Leu Gln Thr Ser Thr Pro Gly Ile Ile
 65                  70                  75                  80

Pro Pro Ala Asp His Pro Ser Gly Tyr Gly Ala Leu Asp Gly Cys
                 85                  90                  95

Pro Ala Gly Tyr Phe Leu Ser Ser Gly His Thr Arg Pro Asp Gly Ala
                100                 105                 110

Pro Ala Leu Glu Ser Pro Arg Ile Glu Ile Thr Ser Cys Leu Gly Leu
            115                 120                 125

Tyr His Asn Asn Asn Gln Phe Phe His Asp Val Glu Val Glu Asp Val
        130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
        195                 200                 205

Cys Val Ser Pro Lys Thr Thr Asp Pro Glu Glu Gly Phe Pro Arg Gly
210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
        275                 280                 285

Gly Ser Pro Arg Val Ser Val Thr Asp Asp Ser Trp Leu Gly Asn Thr
290                 295                 300

Thr Gln Tyr Thr Ser Ser Ala Ile Val Ala Ala Ile Asn Ala Leu Thr
305                 310                 315                 320

Thr Asp Ser Ser Leu Asp Leu Gly Asp Gly Val Pro Val Lys Ser Arg
            325                 330                 335

Lys Thr Thr Leu Glu Gln Pro Pro Ser Val Ala Leu Lys Val Glu Pro
        340                 345                 350

Val Gly Glu Asp Leu Gly Ser Pro Pro Pro Ala Asp Phe Ala Pro
355                 360                 365

Glu Asp Tyr Ser Ser Phe Gln His Ile Arg Lys Gly Gly Phe Cys Asp
370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
                405                 410                 415

Trp Gln Leu Pro Ser His Ser Gly Pro Tyr Glu Leu Arg Ile Glu Val
            420                 425                 430

Gln Pro Lys Ser His His Arg Ala His Tyr Glu Thr Glu Gly Ser Arg
        435                 440                 445

Gly Ala Val Lys Ala Ser Ala Gly Gly His Pro Ile Val Gln Leu His
450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
```

```
                    485                 490                 495
Ile Thr Gly Lys Thr Val Ser Thr Ser His Glu Ala Ile Leu Ser
                500                 505                 510

Asn Thr Lys Val Leu Glu Ile Pro Leu Leu Pro Glu Asn Ser Met Arg
            515                 520                 525

Ala Val Ile Asp Cys Ala Cys Ile Leu Lys Leu Arg Asn Ser Asp Ile
        530                 535                 540

Glu Leu Arg Lys Gly Glu Thr Asp Ile Gly Arg Lys Asn Thr Arg Val
545                 550                 555                 560

Arg Leu Val Phe Arg Val His Val Pro Gln Pro Ser Gly Arg Thr Leu
                565                 570                 575

Ser Leu Gln Val Ala Ser Asn Pro Ile Glu Cys Ser Gln Arg Ser Ala
            580                 585                 590

Gln Glu Leu Pro Leu Val Glu Lys Gln Ser Thr Asp Ser Tyr Pro Val
        595                 600                 605

Val Gly Gly Lys Lys Met Val Leu Ser Gly His Asn Phe Leu Gln Asp
610                 615                 620

Ser Lys Val Ile Phe Val Glu Lys Ala Pro Asp Gly His His Val Trp
625                 630                 635                 640

Glu Met Glu Ala Lys Thr Asp Arg Asp Leu Cys Lys Pro Asn Ser Leu
                645                 650                 655

Val Val Glu Ile Pro Pro Phe Arg Asn Gln Arg Ile Thr Ser Pro Val
            660                 665                 670

His Val Ser Phe Tyr Val Cys Asn Gly Lys Arg Lys Arg Ser Gln Tyr
        675                 680                 685

Gln Arg Phe Thr Tyr Leu Pro Ala Asn Gly Asn Ala Ile Phe Leu Thr
    690                 695                 700

Val Ser Arg Glu His Glu Arg Val Gly Cys Phe Phe
705                 710                 715

<210> SEQ ID NO 39
<211> LENGTH: 30
<212> TYPE: DNA
<213> ORGANISM: Homo sapiens

<400> SEQUENCE: 39
acgcccaaag aggaaaattt gtttcataca                                    30

<210> SEQ ID NO 40
<211> LENGTH: 9
<212> TYPE: PRT
<213> ORGANISM: Homo sapiens

<400> SEQUENCE: 40

Leu Arg Asn Ala Asp Ile Glu Leu Arg
  1               5

<210> SEQ ID NO 41
<211> LENGTH: 6
<212> TYPE: PRT
<213> ORGANISM: Homo sapiens

<400> SEQUENCE: 41

Gly Glu Thr Asp Ile Gly
  1               5

<210> SEQ ID NO 42
<211> LENGTH: 6
```

```
<212> TYPE: PRT
<213> ORGANISM: Homo sapiens

<400> SEQUENCE: 42

Arg Asn Ala Asp Ile Glu
 1               5

<210> SEQ ID NO 43
<211> LENGTH: 18
<212> TYPE: DNA
<213> ORGANISM: Homo sapiens
<220> FEATURE:
<221> NAME/KEY: modified_base
<222> LOCATION: (1)..(18)
<223> OTHER INFORMATION: "n" bases represent inosine

<400> SEQUENCE: 43
mgnaaygcng ayathgar                                             18

<210> SEQ ID NO 44
<211> LENGTH: 18
<212> TYPE: DNA
<213> ORGANISM: Homo sapiens
<220> FEATURE:
<221> NAME/KEY: modified_base
<222> LOCATION: (1)..(18)
<223> OTHER INFORMATION: "n" bases represent inosine

<400> SEQUENCE: 44
nccdatrtcn gtytcncc                                             18

<210> SEQ ID NO 45
<211> LENGTH: 2751
<212> TYPE: DNA
<213> ORGANISM: Homo sapiens
<220> FEATURE:
<221> NAME/KEY: CDS
<222> LOCATION: (240)..(2387)

<400> SEQUENCE: 45
gaattccgca gggcgcgggc accggggcgc gggcagggct cggagccacc gcgcaggtcc    60
tagggccgcg gccgggcccc gccacgcgcg cacacgcccc tcgatgactt tcctccgggg   120
cgcgcggcgc tgagcccggg gcgagggctg tcttcccgga gacccgaccc cggcagcgcg   180
gggcggccat ttctcctgtg cctccgcccg ctgctccact cccgccgcc  gccgcgcgg    239 atg cca agc acc agc ttt cca gtc cct tcc aag ttt cca ctt ggc cct    287
Met Pro Ser Thr Ser Phe Pro Val Pro Ser Lys Phe Pro Leu Gly Pro
 1               5                  10                  15 gag gct gcg gtc ttc ggg aga gga gaa act ttg ggg ccc gcg ccg cgc    335
Glu Ala Ala Val Phe Gly Arg Gly Glu Thr Leu Gly Pro Ala Pro Arg
             20                  25                  30 gcc ggc ggc acc atg aag tca gcg gag gaa gaa cac tat ggc tat gca    383
Ala Gly Gly Thr Met Lys Ser Ala Glu Glu Glu His Tyr Gly Tyr Ala
         35                  40                  45 tcc tcc aac gtc agc ccc gcc ctg ccg ctc ccc acg gcg cac tcc acc    431
Ser Ser Asn Val Ser Pro Ala Leu Pro Leu Pro Thr Ala His Ser Thr
     50                  55                  60 ctg ccg gcc ccg tgc cac aac ctt cag acc tcc aca ccg ggc atc atc    479
Leu Pro Ala Pro Cys His Asn Leu Gln Thr Ser Thr Pro Gly Ile Ile
 65                  70                  75                  80 ccg ccg gcg gac cac ccc tcg ggg tac gga gca gct ttg gac ggt ggg    527
Pro Pro Ala Asp His Pro Ser Gly Tyr Gly Ala Ala Leu Asp Gly Gly
                 85                  90                  95
```

```
ccc gcg ggc tac ttc ctc tcc tcc ggc cac acc agg cct gat cgg gcc        575
Pro Ala Gly Tyr Phe Leu Ser Ser Gly His Thr Arg Pro Asp Arg Ala
            100                 105                 110 cct gcc ctg gag agt cct cgc atc gag ata acc tcg tgc ttg ggc ctg        623
Pro Ala Leu Glu Ser Pro Arg Ile Glu Ile Thr Ser Cys Leu Gly Leu
        115                 120                 125 tac cac aac aat aac cag ttt ttc cac gat gtg gag gtg gaa gac gtc        671
Tyr His Asn Asn Asn Gln Phe Phe His Asp Val Glu Val Glu Asp Val
130                 135                 140 ctc cct agc tcc aaa cgg tcc ccc tcc acg gcc acg ctg agt ctg ccc        719
Leu Pro Ser Ser Lys Arg Ser Pro Ser Thr Ala Thr Leu Ser Leu Pro
145                 150                 155                 160 agc ctg gag gcc tac aga gac ccc tcg tgc ctg agc ccg gcc agc agc        767
Ser Leu Glu Ala Tyr Arg Asp Pro Ser Cys Leu Ser Pro Ala Ser Ser
                165                 170                 175 ctg tcc tcc cgg agc tgc aac tca gag gcc tcc tcc tac gag tcc aac        815
Leu Ser Ser Arg Ser Cys Asn Ser Glu Ala Ser Ser Tyr Glu Ser Asn
            180                 185                 190 tac tcg tac ccg tac gcg tcc ccc cag acg tcg cca tgg cag tct ccc        863
Tyr Ser Tyr Pro Tyr Ala Ser Pro Gln Thr Ser Pro Trp Gln Ser Pro
        195                 200                 205 tgc gtg tct ccc aag acc acg gac ccc gag gag ggc ttt ccc cgc ggg        911
Cys Val Ser Pro Lys Thr Thr Asp Pro Glu Glu Gly Phe Pro Arg Gly
210                 215                 220 ctg ggg gcc tgc aca ctg ctg ggt tcc ccg cag cac tcc ccc tcc acc        959
Leu Gly Ala Cys Thr Leu Leu Gly Ser Pro Gln His Ser Pro Ser Thr
225                 230                 235                 240 tcg ccc cgc gcc agc gtc act gag gag agc tgg ctg ggt gcc cgc tcc       1007
Ser Pro Arg Ala Ser Val Thr Glu Glu Ser Trp Leu Gly Ala Arg Ser
                245                 250                 255 tcc aga ccc gcg tcc cct tgc aac aag agg aag tac agc ctc aac ggc       1055
Ser Arg Pro Ala Ser Pro Cys Asn Lys Arg Lys Tyr Ser Leu Asn Gly
            260                 265                 270 cgg cag ccg ccc tac tca ccc cac cac tcg ccc acg ccg tcc ccg cac       1103
Arg Gln Pro Pro Tyr Ser Pro His His Ser Pro Thr Pro Ser Pro His
        275                 280                 285 ggc tcc ccg agg gtc agc gtg acc gac gac tcg tgg ttg ggc aac acc       1151
Gly Ser Pro Arg Val Ser Val Thr Asp Asp Ser Trp Leu Gly Asn Thr
290                 295                 300 acc cag tac acc agc tcg gcc atc gtg gcc gcc atc aac gag ctg acc       1199
Thr Gln Tyr Thr Ser Ser Ala Ile Val Ala Ala Ile Asn Glu Leu Thr
305                 310                 315                 320 acc gac agc agc ctg gac ctg gga gat ggc gtc cct gtc aag tcc cgc       1247
Thr Asp Ser Ser Leu Asp Leu Gly Asp Gly Val Pro Val Lys Ser Arg
                325                 330                 335 aag acc acc ctg gag cag cag ccc tca gtg gcg ctc aag gtg gag ccc       1295
Lys Thr Thr Leu Glu Gln Gln Pro Ser Val Ala Leu Lys Val Glu Pro
            340                 345                 350 gtc ggg gag gac ctg ggc agc ccc ccg ccg ccg gac ttc gcg ccc           1343
Val Gly Glu Asp Leu Gly Ser Pro Pro Pro Pro Ala Asp Phe Ala Pro
        355                 360                 365 gaa gac tac tcc tct ttc cag cac atc agg aag ggc ggc ttc tgc gac       1391
Glu Asp Tyr Ser Ser Phe Gln His Ile Arg Lys Gly Gly Phe Cys Asp
370                 375                 380 cag tac ctg gcg gtg ccg cag cac ccc tac cag tgg gcg aag ccc aag       1439
Gln Tyr Leu Ala Val Pro Gln His Pro Tyr Gln Trp Ala Lys Pro Lys
385                 390                 395                 400 ccc ctg tcc cct acg tcc tac atg agc ccg acc ctg ccc gcc ctg gac       1487
Pro Leu Ser Pro Thr Ser Tyr Met Ser Pro Thr Leu Pro Ala Leu Asp
                405                 410                 415
```

-continued

| | |
|---|---|
| tgg cag ctg ccg tcc cac tca ggc ccg tat gag ctt cgg att gag gtg<br>Trp Gln Leu Pro Ser His Ser Gly Pro Tyr Glu Leu Arg Ile Glu Val<br>                420                           425                       430 | 1535 |
| cag ccc aag tcc cac cac cga gcc cac tac gag acg gag ggc agc cgg<br>Gln Pro Lys Ser His His Arg Ala His Tyr Glu Thr Glu Gly Ser Arg<br>                435                           440                       445 | 1583 |
| ggg gca gtg aag gcg tcg gcc gga gga cac ccc atc gtg cag ctg cat<br>Gly Ala Val Lys Ala Ser Ala Gly Gly His Pro Ile Val Gln Leu His<br>450                           455                           460 | 1631 |
| ggc tac ttg gag aat gag ccg ctg atg ctg cag ctt ttc att ggg acg<br>Gly Tyr Leu Glu Asn Glu Pro Leu Met Leu Gln Leu Phe Ile Gly Thr<br>465                         470                         475                  480 | 1679 |
| gcg gac gac cgc ctg ctg cgc ccg cac gcc ttc tac cag gtg cac cgc<br>Ala Asp Asp Arg Leu Leu Arg Pro His Ala Phe Tyr Gln Val His Arg<br>                      485                           490                       495 | 1727 |
| atc aca ggg aag acc gtg tcc acc acc agc cac gag gct atc ctc tcc<br>Ile Thr Gly Lys Thr Val Ser Thr Thr Ser His Glu Ala Ile Leu Ser<br>                500                           505                       510 | 1775 |
| aac acc aaa gtc ctg gag atc cca ctc ctg ccg gag aac agc atg cga<br>Asn Thr Lys Val Leu Glu Ile Pro Leu Leu Pro Glu Asn Ser Met Arg<br>515                         520                         525 | 1823 |
| gcc gtc att gac tgt gcc gga atc ctg aaa ctc aga aac tcc gac att<br>Ala Val Ile Asp Cys Ala Gly Ile Leu Lys Leu Arg Asn Ser Asp Ile<br>                530                           535                       540 | 1871 |
| gaa ctt cgc aaa gga gag acg gac atc ggg agg aag aac aca cgg gta<br>Glu Leu Arg Lys Gly Glu Thr Asp Ile Gly Arg Lys Asn Thr Arg Val<br>545                         550                         555                  560 | 1919 |
| cgg ctg gtg ttc cgc gtt cac gtc ccg caa ccc agc ggc cgc acg ctg<br>Arg Leu Val Phe Arg Val His Val Pro Gln Pro Ser Gly Arg Thr Leu<br>                      565                           570                       575 | 1967 |
| tcc ctg cag gtg gcc tcc aac ccc atc gaa tgc tcc cag cgc tca gct<br>Ser Leu Gln Val Ala Ser Asn Pro Ile Glu Cys Ser Gln Arg Ser Ala<br>                580                           585                       590 | 2015 |
| cag gag ctg cct ctg gtg gag aag cag agc acg gac agc tat ccg gtc<br>Gln Glu Leu Pro Leu Val Glu Lys Gln Ser Thr Asp Ser Tyr Pro Val<br>595                         600                         605 | 2063 |
| gtg ggc ggg aag aag atg gtc ctg tct ggc cac aac ttc ctg cag gac<br>Val Gly Gly Lys Lys Met Val Leu Ser Gly His Asn Phe Leu Gln Asp<br>610                         615                         620 | 2111 |
| tcc aag gtc att ttc gtg gag aaa gcc cca gat ggc cac cat gtc tgg<br>Ser Lys Val Ile Phe Val Glu Lys Ala Pro Asp Gly His His Val Trp<br>625                         630                         635                  640 | 2159 |
| gag atg gaa gcg aaa act gac cgg gac ctg tgc aag ccg aat tct ctg<br>Glu Met Glu Ala Lys Thr Asp Arg Asp Leu Cys Lys Pro Asn Ser Leu<br>                      645                           650                       655 | 2207 |
| gtg gtt gag atc ccg cca ttt cgg aat cag agg ata acc agc ccc gtt<br>Val Val Glu Ile Pro Pro Phe Arg Asn Gln Arg Ile Thr Ser Pro Val<br>                660                           665                       670 | 2255 |
| cac gtc agt ttc tac gtc tgc aac ggg aag aga aag gga agc cag tac<br>His Val Ser Phe Tyr Val Cys Asn Gly Lys Arg Lys Gly Ser Gln Tyr<br>675                         680                         685 | 2303 |
| cag cgt ttc acc tac ctt ccc gcc aac ggt aac gcc atc ttt cta acc<br>Gln Arg Phe Thr Tyr Leu Pro Ala Asn Gly Asn Ala Ile Phe Leu Thr<br>                      690                           695                       700 | 2351 |
| gta agc cgt gaa cat gag cgc gtg ggg tgc ttt ttc taaagacgca<br>Val Ser Arg Glu His Glu Arg Val Gly Cys Phe Phe<br>705                         710                         715 | 2397 |
| gaaacgacgt cgccgtaaag cagcgtggcg tgttgcacat ttaactgtgt gatgtcccgt | 2457 |

-continued

```
tagtgagacc gagccatcga tgccctgaaa aggaaaggaa aagggaagct tcggatgcat    2517
tttccttgat ccctgttggg ggtgggggc ggggttgca tactcagata gtcacggtta    2577
ttttgcttct tgcgaatgta taacagccaa ggggaaaaca tggctcttct gctccaaaaa    2637
actgaggggg tcctggtgtg catttgcacc ctaaagctgc ttacggtgaa aaggcaaata    2697
ggtatagcta ttttgcaggc acctttagga ataaactttg cttttaaaaa aaaa         2751
```

<210> SEQ ID NO 46
<211> LENGTH: 716
<212> TYPE: PRT
<213> ORGANISM: Homo sapiens

<400> SEQUENCE: 46

```
Met Pro Ser Thr Ser Phe Pro Val Pro Ser Lys Phe Pro Leu Gly Pro
 1               5                  10                  15

Glu Ala Ala Val Phe Gly Arg Gly Glu Thr Leu Gly Pro Ala Pro Arg
            20                  25                  30

Ala Gly Gly Thr Met Lys Ser Ala Glu Glu His Tyr Gly Tyr Ala
        35                  40                  45

Ser Ser Asn Val Ser Pro Ala Leu Pro Leu Pro Thr Ala His Ser Thr
    50                  55                  60

Leu Pro Ala Pro Cys His Asn Leu Gln Thr Ser Thr Pro Gly Ile Ile
65                  70                  75                  80

Pro Pro Ala Asp His Pro Ser Gly Tyr Gly Ala Ala Leu Asp Gly Gly
                85                  90                  95

Pro Ala Gly Tyr Phe Leu Ser Ser Gly His Thr Arg Pro Asp Arg Ala
            100                 105                 110

Pro Ala Leu Glu Ser Pro Arg Ile Glu Ile Thr Ser Cys Leu Gly Leu
        115                 120                 125

Tyr His Asn Asn Gln Phe Phe His Asp Val Glu Val Glu Asp Val
    130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Ser Pro Gln Thr Ser Pro Trp Gln Ser Pro
        195                 200                 205

Cys Val Ser Pro Lys Thr Thr Asp Pro Glu Glu Gly Phe Pro Arg Gly
    210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
        275                 280                 285

Gly Ser Pro Arg Val Ser Val Thr Asp Asp Ser Trp Leu Gly Asn Thr
    290                 295                 300

Thr Gln Tyr Thr Ser Ser Ala Ile Val Ala Ala Ile Asn Glu Leu Thr
305                 310                 315                 320

Thr Asp Ser Ser Leu Asp Leu Gly Asp Gly Val Pro Val Lys Ser Arg
```

-continued

```
                      325                 330                 335
Lys Thr Thr Leu Glu Gln Gln Pro Ser Val Ala Leu Lys Val Glu Pro
                    340                 345                 350

Val Gly Glu Asp Leu Gly Ser Pro Pro Pro Ala Asp Phe Ala Pro
                355                 360                 365

Glu Asp Tyr Ser Ser Phe Gln His Ile Arg Lys Gly Gly Phe Cys Asp
            370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
                405                 410                 415

Trp Gln Leu Pro Ser His Ser Gly Pro Tyr Glu Leu Arg Ile Glu Val
                420                 425                 430

Gln Pro Lys Ser His His Arg Ala His Tyr Glu Thr Glu Gly Ser Arg
                435                 440                 445

Gly Ala Val Lys Ala Ser Ala Gly Gly His Pro Ile Val Gln Leu His
450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
                485                 490                 495

Ile Thr Gly Lys Thr Val Ser Thr Ser His Glu Ala Ile Leu Ser
                500                 505                 510

Asn Thr Lys Val Leu Glu Ile Pro Leu Leu Pro Glu Asn Ser Met Arg
                515                 520                 525

Ala Val Ile Asp Cys Ala Gly Ile Leu Lys Leu Arg Asn Ser Asp Ile
                530                 535                 540

Glu Leu Arg Lys Gly Glu Thr Asp Ile Gly Arg Lys Asn Thr Arg Val
545                 550                 555                 560

Arg Leu Val Phe Arg Val His Val Pro Gln Pro Ser Gly Arg Thr Leu
                565                 570                 575

Ser Leu Gln Val Ala Ser Asn Pro Ile Glu Cys Ser Gln Arg Ser Ala
                580                 585                 590

Gln Glu Leu Pro Leu Val Glu Lys Gln Ser Thr Asp Ser Tyr Pro Val
                595                 600                 605

Val Gly Gly Lys Lys Met Val Leu Ser Gly His Asn Phe Leu Gln Asp
                610                 615                 620

Ser Lys Val Ile Phe Val Glu Lys Ala Pro Asp Gly His His Val Trp
625                 630                 635                 640

Glu Met Glu Ala Lys Thr Asp Arg Asp Leu Cys Lys Pro Asn Ser Leu
                645                 650                 655

Val Val Glu Ile Pro Pro Phe Arg Asn Gln Arg Ile Thr Ser Pro Val
                660                 665                 670

His Val Ser Phe Tyr Val Cys Asn Gly Lys Arg Lys Gly Ser Gln Tyr
                675                 680                 685

Gln Arg Phe Thr Tyr Leu Pro Ala Asn Gly Asn Ala Ile Phe Leu Thr
                690                 695                 700

Val Ser Arg Glu His Glu Arg Val Gly Cys Phe Phe
705                 710                 715

<210> SEQ ID NO 47
<211> LENGTH: 302
<212> TYPE: PRT
<213> ORGANISM: Drosophila sp.
```

-continued

```
<400> SEQUENCE: 47

Thr Lys Asn Val Arg Lys Pro Tyr Val Lys Ile Thr Glu Gln Pro
  1               5                  10                  15

Ala Gly Lys Ala Leu Arg Phe Arg Tyr Glu Cys Glu Gly Arg Ser Ala
                 20                  25                  30

Gly Ser Ile Pro Gly Val Asn Ser Thr Pro Glu Asn Lys Thr Tyr Pro
             35                  40                  45

Thr Ile Glu Ile Val Gly Tyr Lys Gly Arg Ala Val Val Val Ser
     50                  55                  60

Cys Val Thr Lys Asp Thr Pro Tyr Arg Pro His Pro His Asn Leu Val
 65                  70                  75                  80

Gly Lys Glu Gly Cys Lys Lys Gly Val Cys Thr Leu Glu Ile Asn Ser
                 85                  90                  95

Glu Thr Met Arg Ala Val Phe Ser Asn Leu Gly Ile Gln Cys Val Lys
                100                 105                 110

Lys Lys Asp Ile Glu Ala Ala Leu Lys Ala Arg Glu Glu Ile Arg Val
            115                 120                 125

Asp Pro Phe Lys Thr Gly Phe Ser His Arg Phe Gln Pro Ser Ser Ile
        130                 135                 140

Asp Leu Asn Ser Val Arg Leu Cys Phe Gln Val Phe Met Glu Ser Glu
145                 150                 155                 160

Gln Lys Gly Arg Phe Thr Ser Pro Leu Pro Pro Val Val Ser Glu Pro
                165                 170                 175

Ile Phe Asp Lys Lys Ala Met Ser Asp Leu Val Ile Cys Arg Leu Cys
            180                 185                 190

Ser Cys Ser Ala Thr Val Phe Gly Asn Thr Gln Ile Ile Leu Leu Cys
        195                 200                 205

Glu Lys Val Ala Lys Glu Asp Ile Ser Val Arg Phe Glu Glu Lys
    210                 215                 220

Asn Gly Gln Ser Val Trp Glu Ala Phe Gly Asp Phe Gln His Thr Asp
225                 230                 235                 240

Val His Lys Gln Thr Ala Ile Thr Phe Lys Thr Pro Arg Tyr His Thr
                245                 250                 255

Leu Asp Ile Thr Glu Pro Ala Lys Val Phe Ile Gln Leu Arg Arg Pro
            260                 265                 270

Ser Asp Gly Val Thr Ser Glu Ala Leu Pro Phe Glu Tyr Val Pro Met
        275                 280                 285

Asp Ser Asp Pro Ala His Leu Arg Arg Lys Arg Gln Lys Thr
    290                 295                 300

<210> SEQ ID NO 48
<211> LENGTH: 296
<212> TYPE: PRT
<213> ORGANISM: Homo sapiens

<400> SEQUENCE: 48

Met Ala Ser Gly Leu Tyr Asn Pro Tyr Ile Glu Ile Ile Glu Gln Pro
  1               5                  10                  15

Arg Gln Arg Gly Met Arg Phe Arg Tyr Lys Cys Glu Gly Arg Ser Ala
                 20                  25                  30

Gly Ser Ile Pro Gln Glu His Ser Thr Asp Asn Asn Arg Thr Tyr Pro
             35                  40                  45

Ser Ile Asn Ile Met Asn Tyr Tyr Gly Arg Gly Lys Val Arg Ile Thr
     50                  55                  60
```

Leu Val Thr Lys Asn Asp Pro Tyr Lys Pro His Pro His Asp Leu Val
65                  70                  75                  80

Gly Lys Asp Cys Arg Asp Gly Tyr Tyr Glu Ala Glu Phe Gly Asn Glu
            85                  90                  95

Arg Arg Pro Leu Phe Gln Asn Leu Gly Ile Arg Cys Val Lys Lys
        100                 105                 110

Lys Glu Val Lys Glu Ala Ile Ile Thr Arg Ile Lys Ala Gly Ile Asn
        115                 120                 125

Pro Phe Asn Val Pro Glu Lys Gln Leu Asn Asp Ile Glu Asp Cys Asp
        130                 135                 140

Leu Asn Val Val Arg Leu Cys Phe Gln Val Phe Leu Pro Asp Glu His
145                 150                 155                 160

Gly Asn Leu Thr Thr Ala Leu Pro Pro Val Val Ser Asn Pro Ile Tyr
            165                 170                 175

Asp Asn Arg Ala Pro Asn Thr Ala Glu Leu Arg Ile Cys Arg Val Asn
            180                 185                 190

Lys Asn Cys Gly Ser Val Arg Gly Gly Asp Glu Ile Phe Leu Leu Cys
        195                 200                 205

Asp Lys Val Gln Lys Asp Asp Ile Glu Val Arg Phe Val Leu Asn Asp
        210                 215                 220

Trp Glu Ala Lys Gly Ile Phe Ser Gln Ala Asp Val His Arg Gln Val
225                 230                 235                 240

Ala Ile Val Phe Lys Thr Pro Pro Tyr Cys Lys Ala Ile Thr Glu Pro
                245                 250                 255

Val Thr Val Lys Met Gln Leu Arg Arg Pro Ser Asp Gln Glu Val Ser
            260                 265                 270

Glu Ser Met Asp Phe Arg Tyr Leu Pro Asp Glu Lys Asp Thr Tyr Gly
        275                 280                 285

Asn Lys Ala Lys Lys Gln Lys Thr
        290                 295

<210> SEQ ID NO 49
<211> LENGTH: 332
<212> TYPE: PRT
<213> ORGANISM: Homo sapiens

<400> SEQUENCE: 49

Ile Pro Leu Ser Thr Asp Gly Pro Tyr Leu Gln Ile Leu Glu Gln Pro
1               5                   10                  15

Lys Gln Arg Gly Phe Arg Phe Arg Tyr Val Cys Glu Gly Pro Ser His
            20                  25                  30

Gly Gly Leu Pro Gly Ala Ser Ser Glu Lys Asn Lys Lys Ser Tyr Pro
        35                  40                  45

Gln Val Lys Ile Cys Asn Tyr Val Gly Pro Ala Lys Val Ile Val Gln
    50                  55                  60

Leu Val Thr Asn Gly Lys Asn Ile His Leu His Ala His Ser Leu Val
65                  70                  75                  80

Gly Lys His Cys Glu Asp Gly Val Cys Thr Val Thr Ala Gly Pro Lys
            85                  90                  95

Asp Met Val Val Gly Phe Ala Asn Leu Gly Ile Leu His Val Thr Lys
        100                 105                 110

Lys Lys Val Phe Glu Thr Leu Glu Ala Arg Met Thr Glu Ala Cys Ile
        115                 120                 125

Arg Gly Tyr Asn Pro Gly Leu Leu Val His Ser Asp Leu Ala Tyr Leu

-continued

```
             130                 135                 140
Gln Ala Glu Gly Gly Gly Asp Arg Gln Leu Thr Asp Arg Glu Lys Glu
145                 150                 155                 160
Ile Ile Arg Gln Ala Ala Val Gln Gln Thr Lys Glu Met Asp Leu Ser
                165                 170                 175
Val Val Arg Leu Met Phe Thr Ala Phe Leu Pro Asp Ser Thr Gly Ser
                180                 185                 190
Phe Thr Arg Arg Leu Glu Pro Val Val Ser Asp Ala Ile Tyr Asp Ser
                195                 200                 205
Lys Ala Pro Asn Ala Ser Asn Leu Lys Ile Val Arg Met Asp Arg Thr
                210                 215                 220
Ala Gly Cys Val Thr Gly Gly Glu Glu Ile Tyr Leu Leu Cys Asp Lys
225                 230                 235                 240
Val Gln Lys Asp Asp Ile Gln Ile Arg Phe Tyr Glu Glu Glu Asn
                245                 250                 255
Gly Gly Val Trp Glu Gly Phe Gly Asp Phe Ser Pro Thr Asp Val His
                260                 265                 270
Arg Gln Phe Ala Ile Val Phe Lys Thr Pro Lys Tyr Lys Asp Val Asn
                275                 280                 285
Ile Thr Lys Pro Ala Ser Val Phe Val Gln Leu Arg Arg Lys Ser Asp
290                 295                 300
Leu Glu Thr Ser Glu Pro Lys Pro Phe Leu Tyr Tyr Pro Glu Ile Lys
305                 310                 315                 320
Asp Lys Glu Glu Val Gln Arg Lys Arg Gln Lys Leu
                325                 330
```

<210> SEQ ID NO 50
<211> LENGTH: 295
<212> TYPE: PRT
<213> ORGANISM: Homo sapiens

<400> SEQUENCE: 50

```
Glu Pro Ala Gln Ala Ser Gly Pro Tyr Val Glu Ile Ile Glu Gln Pro
 1               5                  10                  15
Lys Gln Arg Gly Met Arg Phe Arg Tyr Lys Cys Glu Gly Arg Ser Ala
                20                  25                  30
Gly Ser Ile Pro Gly Glu Arg Ser Thr Asp Thr Thr Lys Thr His Pro
                35                  40                  45
Thr Ile Lys Ile Asn Gly Tyr Thr Gly Pro Gly Thr Val Arg Ile Ser
            50                  55                  60
Leu Val Thr Lys Asp Pro Pro His Arg Pro His Pro His Glu Leu Val
65                  70                  75                  80
Gly Lys Asp Cys Arg Asp Gly Tyr Tyr Glu Ala Asp Leu Cys Pro Asp
                85                  90                  95
Arg Asp Ser Ile His Ser Phe Gln Asn Leu Gly Ile Gln Cys Val Lys
                100                 105                 110
Lys Arg Asp Leu Glu Gln Ala Ile Ser Gln Arg Ile Gln Thr Asn Asn
                115                 120                 125
Asn Pro Phe His Val Pro Ile Glu Glu Gln Arg Gly Asp Tyr Asp Leu
                130                 135                 140
Asn Ala Val Arg Leu Cys Phe Gln Val Thr Val Arg Asp Pro Ala Gly
145                 150                 155                 160
Arg Pro Leu Leu Leu Thr Pro Val Leu Ser His Pro Ile Phe Asp Asn
                165                 170                 175
```

-continued

```
Arg Ala Pro Asn Thr Ala Glu Leu Lys Ile Cys Arg Val Asn Arg Asn
            180                 185                 190

Ser Gly Ser Cys Leu Gly Gly Asp Glu Ile Phe Leu Leu Cys Asp Lys
        195                 200                 205

Val Gln Lys Glu Asp Ile Glu Val Tyr Phe Thr Gly Pro Gly Trp Glu
    210                 215                 220

Ala Arg Gly Ser Phe Ser Gln Ala Asp Val His Arg Gln Val Ala Ile
225                 230                 235                 240

Val Phe Arg Thr Pro Pro Tyr Ala Asp Pro Ser Leu Gln Ala Pro Val
                245                 250                 255

Arg Val Ser Met Gln Leu Arg Arg Pro Ser Asp Arg Glu Leu Ser Glu
            260                 265                 270

Pro Met Glu Phe Gln Tyr Leu Pro Asp Thr Asp Asp Arg His Arg Ile
        275                 280                 285

Glu Glu Lys Arg Lys Arg Thr
        290                 295
```

<210> SEQ ID NO 51
<211> LENGTH: 293
<212> TYPE: PRT
<213> ORGANISM: Homo sapiens

<400> SEQUENCE: 51

```
Gln Leu Pro Ser His Ser Gly Pro Tyr Glu Leu Arg Ile Glu Val Gln
1               5                   10                  15

Pro Lys Ser His His Arg Ala His Tyr Glu Thr Glu Gly Ser Arg Gly
            20                  25                  30

Ala Val Lys Ala Ser Ala Gly Gly His Pro Ile Val Gln Leu His Gly
        35                  40                  45

Tyr Leu Glu Asn Glu Pro Leu Met Leu Gln Leu Phe Ile Gly Thr Ala
    50                  55                  60

Asp Asp Arg Leu Leu Arg Pro His Ala Phe Tyr Gln Val His Arg Ile
65                  70                  75                  80

Thr Gly Lys Thr Val Ser Thr Thr Ser His Glu Ala Ile Leu Ser Asn
                85                  90                  95

Thr Lys Val Leu Glu Ile Pro Leu Leu Pro Glu Asn Ser Met Arg Ala
            100                 105                 110

Val Ile Asp Cys Ala Gly Ile Leu Lys Leu Arg Asn Ser Asp Ile Glu
        115                 120                 125

Leu Arg Lys Gly Glu Thr Asp Ile Gly Arg Lys Asn Thr Arg Val Arg
    130                 135                 140

Leu Val Phe Arg Val His Val Pro Gln Pro Ser Gly Arg Thr Leu Ser
145                 150                 155                 160

Leu Gln Val Ala Ser Asn Pro Ile Glu Cys Ser Gln Arg Ser Ala Gln
                165                 170                 175

Glu Leu Pro Leu Val Glu Lys Gln Ser Thr Asp Ser Tyr Pro Val Val
            180                 185                 190

Gly Gly Lys Lys Met Val Leu Ser Gly His Asn Phe Leu Gln Asp Ser
        195                 200                 205

Lys Val Ile Phe Val Glu Lys Ala Pro Asp Gly His His Val Trp Glu
    210                 215                 220

Met Glu Ala Lys Thr Asp Arg Asp Leu Cys Lys Pro Asn Ser Leu Val
225                 230                 235                 240

Val Glu Ile Pro Pro Phe Arg Asn Gln Arg Ile Thr Ser Pro Val His
                245                 250                 255
```

-continued

```
Val Ser Phe Tyr Val Cys Asn Gly Lys Arg Lys Arg Ser Gln Tyr Gln
            260                 265                 270

Arg Phe Thr Tyr Leu Pro Ala Asn Gly Asn Ala Ile Phe Leu Thr Val
            275                 280                 285

Ser Arg Glu His Glu
        290

<210> SEQ ID NO 52
<211> LENGTH: 293
<212> TYPE: PRT
<213> ORGANISM: Mus sp.

<400> SEQUENCE: 52

Pro Leu Ser Asn Gln Ser Gly Ser Tyr Glu Leu Arg Ile Glu Val Gln
  1               5                  10                  15

Pro Lys Pro His His Arg Ala His Tyr Glu Thr Glu Gly Ser Arg Gly
             20                  25                  30

Ala Val Lys Ala Pro Thr Gly Gly His Pro Val Val Gln Leu His Gly
         35                  40                  45

Tyr Met Glu Asn Lys Pro Leu Gly Leu Gln Ile Phe Ile Gly Thr Ala
     50                  55                  60

Asp Glu Arg Ile Leu Lys Pro His Ala Phe Tyr Gln Val His Arg Ile
 65                  70                  75                  80

Thr Gly Lys Thr Val Thr Thr Thr Ser Tyr Glu Lys Ile Val Gly Asn
                 85                  90                  95

Thr Lys Val Leu Glu Ile Pro Leu Glu Pro Lys Asn Asn Met Arg Ala
            100                 105                 110

Thr Ile Asp Cys Ala Gly Ile Leu Lys Leu Arg Asn Ala Asp Ile Glu
        115                 120                 125

Leu Arg Lys Gly Glu Thr Asp Ile Gly Arg Lys Asn Thr Arg Val Arg
    130                 135                 140

Leu Val Phe Arg Val His Val Pro Glu Pro Ser Gly Arg Ile Val Ser
145                 150                 155                 160

Leu Gln Ala Ala Ser Asn Pro Ile Glu Cys Ser Gln Arg Ser Ala His
                165                 170                 175

Glu Leu Pro Met Val Glu Arg Gln Asp Met Asp Ser Cys Leu Val Tyr
            180                 185                 190

Gly Gly Gln Gln Met Ile Leu Thr Gly Gln Asn Phe Thr Ala Glu Ser
        195                 200                 205

Lys Val Val Phe Met Glu Lys Thr Thr Asp Gly Gln Gln Ile Trp Glu
    210                 215                 220

Met Glu Ala Thr Val Asp Lys Asp Lys Ser Gln Pro Asn Met Leu Phe
225                 230                 235                 240

Val Glu Ile Pro Glu Tyr Arg Asn Lys His Ile Arg Val Pro Val Lys
                245                 250                 255

Val Asn Phe Tyr Val Ile Asn Gly Lys Arg Lys Arg Ser Gln Pro Gln
            260                 265                 270

His Phe Thr Tyr His Pro Val Pro Ala Ile Lys Thr Glu Pro Ser Asp
        275                 280                 285

Glu Tyr Glu Pro Ser
    290
```

NF-AT POLYPEPTIDES AND POLYNUCLEOTIDES

This application is a continuation application of Ser. No. 08/260,174 filed on Jun. 13, 1994, U.S. Pat. No. 6,197,925 which is a continuation-in-part of U.S. Ser. No. 08/124,981 filed Sep. 20, 1993, U.S. Pat. No. 5,837,840.

STATEMENT OF RIGHTS

This invention was made in the course of work supported by the U.S. Government and Howard Hughes Medical Institute, which may have certain rights in this invention.

FIELD OF THE INVENTION

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

BACKGROUND OF THE INVENTION

The immune response is coordinated by the actions of cytokines produced from activated T lymphocytes. The precursors for most T lymphocytes arise in the bone marrow and migrate to the thymus where they differentiate and express receptors capable of interacting with antigen. These differentiated T lymphocytes then migrate to the peripheral lymphoid organs where they remain quiescent until they come in contact with the cognate antigen. The interaction of antigen with the antigen receptor on T lymphocytes initiates an ordered series of pleiotropic changes; a process denoted as T lymphocyte activation. T lymphocyte activation is a 7 to 10 day process that results in cell division and the acquisition of immunological functions such as cytotoxicity and the production of lymphokines that induce antibody production by B lymphocytes and control the growth and differentiation of granulocyte and macrophage precursors. The cytokines produced by activated T lymphocytes act upon other cells of the immune system to coordinate their behavior and bring about an effective immune response.

The initiation of T lymphocyte activation requires a complex interaction of the antigen receptor with the combination of antigen and self-histocompatibility molecules on the surface of antigen-presenting cells. T lymphocytes may also be activated by relatively simple stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell (1960) *Cancer Res.* 20: 462).

T lymphocyte activation involves the specific regulation of particular subsets of genes. The transcriptional regulation characteristic of T cell activation begins minutes after the antigen encounter and continues until at least 10 days later. The T lymphocyte activation genes can be grouped according to the time after stimulation at which each gene is transcribed. Early genes are the first subset of T lymphocyte activation genes that is expressed during the activation process. Expression of the early genes triggers the transcriptional modulation of subsequent genes in the activation pathway. Because of the critical role of the T lymphocyte in the immune response, agents that interfere with expression of the early activation genes, such as cyclosporin A and FK506, are effective immunosuppressants.

Transcription of the early genes requires the presence of specific transcription factors, such as NF-AT, which in turn are regulated through interactions with the antigen receptor. These transcription factors are proteins which act through enhancer and promoter elements near the early activation genes to modulate the rate of transcription of these genes. Many of these transcription factors reversibly bind to specific DNA sequences located in and near enhancer elements.

The interleukin-2 (IL-2) gene is a paradigmatic early activation gene. The IL-2 gene product plays a critical role in T lymphocyte proliferation and differentiation. The IL-2 gene is transcriptionally active only in T cells that have been stimulated through the antigen receptor or its associated molecules (Cantrell and Smith (1984) *Science* 224: 1312). The transcriptional induction of IL-2 in activated T lymphocytes is mediated by a typical early gene transcriptional enhancer that extends from 325 basepairs upstream of the transcriptional start site for the IL-2 gene (Durand et al. (1988) *Mol. Cell. Biol.* 8: 1715). Other genes known to contain NF-AT recognition sites in their regulatory regions include: γ-interferon, IL-4, GM-CSF, and others. This region, which is referred to herein as the IL-2 enhancer, has been used extensively to dissect the requirements for T lymphocyte activation. An array of transcription factors, including NF-AT, NFkb, AP-1, Oct-1, and a newly identified protein that associates with Oct-1 called OAP-40, bind to sequences in this region (Ullman et al. (1991) *Science* 254: 553). These different transcription factors act together to integrate the complex requirements for T lymphocyte activation.

Among the group of transcription factors mentioned above, the presence of NF-AT is characteristic of the transcription events involving early activation genes, in that its recognition sequence is able to enhance transcription of linked heterologous genes in activated T cells of transgenic animals (Verweij et al. (1990) *J. Biol. Chem.* 265: 15788). The NF-AT sequence element is also the only known transcriptional element in the IL-2 enhancer that has no stimulatory effect on transcription in the absence of physiologic activation of the T lymphocyte through the antigen receptor or through treatment of T cells with the combination of ionomycin and PMA. For example, the NF-AT element enhances transcription of linked sequences in T lymphocytes which have had proper presentation of specific antigen by MHC-matched antigen presenting cells or have been stimulated with the combination of ionomycin/PMA, but not in unstimulated T lymphocytes (Durand et al. (1988) op.cit; Shaw et al. (1988) op.cit; Karttunen and Shastri (1991) *Proc. Natl. Acad. Sci. USA* 88: 3972; Verweij et al. (1990) op.cit). Moreover, the NF-AT sequence element naturally enhances transcription of the IL-2 gene only in activated T lymphocytes.

Other elements within the IL-2 enhancer, for example, the NFkb site or the AP-1 site, activate transcription in response to less specific stimuli, such as tumor necrosis factor a or simply PMA by itself. These compounds do not by themselves activate transcription of the IL-2 gene and other early activation genes, and do not lead to T lymphocyte activation.

Such observations indicate that the expression of certain early genes, such as the interleukin-2 gene may be regulated by the protein complex NF-AT. Data have also indicated that a selective genetic deficiency of NF-AT produces severe combined immunodeficiency (SCID) (Chatilla et al. (1989) *New Enql. J. Med.* 320: 696).

One of the functional sequences in the IL-2 enhancer is a binding site for a multimeric protein complex, designated NF-AT (nuclear factor of activated T lymphocytes), that functions as a transcriptional regulator of IL-2, IL-4, and other early activation genes (Shaw et al. (1988) *Science* 241: 202). The NF-AT transcription complex is formed subsequent to a signal from the antigen receptor. Enhancement of transcription of genes adjacent to the NF-AT recognition site requires that the NF-AT complex bind to the recognition site (Shaw et al. (1988) op.cit). Although the molecular makeup of NF-AT is not fully defined, studies have reported that NF-AT can be reconstituted from a ubiquitous nuclear component that requires protein synthesis for induction and a T cell-specific constitutive cytoplasmic component, designated NF-$AT_c$ (Flanagan et al. (1991) *Nature* 352: 803). This cytoplasmic component, NF-$AT_c$, associates with the nucleus in response to calcium signalling in a manner that is inhibited by the immunosuppressive drugs cyclosporin A (CsA) and FK506. The nuclear component of NF-AT can be induced with PMA, is not sensitive to CsA or FK506, and can be seen in cells of non-T cell origin such as HeLa and Cos.

Northrop et al. (1993) *J. Biol. Chem.* 268: 2917 report that the nuclear component of NF-AT contains the phorbol ester-inducible transcription factor, AP-1 (Jun/Fos), and show that antisera to Fos (a component of AP-1) inhibits NF-AT binding to DNA containing a binding site for AP-1. Moreover, Northrop et al. show that NF-AT DNA binding can be reconstituted in vitro using semi-purified AP-1 proteins mixed with cytosol from T lymphocytes, presumably containing NF-$AT_c$. Northrop et al. also report partial purification of NF-$AT_c$ and report a molecular mass range of approximately 94 to 116 kD as estimated by SDS-polyacrylamide gel electrophoresis.

As noted above, cyclosporin A (CsA) and FK506 are capable of acting as immunosuppressants. These agents inhibit T and B cell activation, mast cell degranulation, and other processes essential to an effective immune response (Borel et al. (1976) *Agents Actions* 6: 468; Sung et al. (1988) *J. Exp. Med.* 168: 1539; Gao et al. *Nature* 336: 176). In T lymphocytes, these drugs disrupt a step in the signal transduction pathway(s) through which the binding of antigen to the T cell antigen receptor produces enhanced transcription of specific cytokine genes involved in the coordination of the immune response. Thus, these agents prevent T lymphocyte activation (Crabtree et al. (1989) *Science* 243: 355; Schreiber et al. (1989) *Science* 251: 283; Hohman & Hutlsch (1990) *New Biol.* 2: 663) and act as immunosuppressants.

Putative intracellular receptors for FK506 and CsA have been described and found to be cis-trans prolyl isomerases (Fischer & Bang (1985) *Biochim. Biophys. Acta* 828: 39; Fischer et al. *Nature* 337: 476; Handschumacher et al. (1984) *Science* 226: 544; Lang & Schmid (1988) *Nature* 331: 453; Standaert et al. (1990) *Nature* 346: 671). Binding of the drugs inhibits isomerase activity; however, studies with other prolyl isomerase inhibitors (Bierer et al. (1990) *Science* 250: 556) and analysis of cyclosporin-resistant mutants in yeast suggest that the prevention of T lymphocyte activation results from formation of an inhibitory complex involving the drug and the isomerase (Bierer et al. (1990) *Proc. Natl. Acad. Sci. U.S.A.* 87: 9231; Tropschug et al. (1989) *Nature* 342: 953), and not from inhibition of the isomerase activity per se. CsA and FK-506 prevent T cell proliferation by inhibiting a calcium-dependent signalling event required for the induction of interleukin-2 transcription.

Calcineurin, a calmodulin-dependent protein phosphatase which occurs in various isoforms, has been identified as a critical component of T cell activation through the signal transduction pathway leading to transcriptional activation of NF-AT-dependent genes, such as lymphokine genes (Liu et al. (1991) *Cell* 66: 807; Clipstone and Crabtree (1992) *Nature* 357: 695; O'Keefe et al. (1992) *Nature* 357: 692)

Transcriptional enhancement involving NF-AT recognition sequences is completely blocked in T cells treated with efficacious concentrations of cyclosporin A or FK506, with little or no specific effect on transcriptional enhancement involving recognition sites for other transcription factors, such as AP-1 and NF-κB (Shaw et al. (1988) op.cit; Emmel et al. (1989) *Science* 246: 1617; Mattila et al. (1990) *EMBO J.* 9: 4425). This blockage can be overcome, at least partially, by the expression of hyperphysiolgical amounts of calcineurin (Clipstone and Crabtree (1992) op.cit.).

Unfortunately, while both cyclosporin A and FK506 are potent immunosuppressive agents, both drugs possess detrimental properties. For example, cyclosporin elicits adverse reactions including renal dysfunction, tremors, nausea and hypertension. Indeed, for many years researchers have attempted to develop superior replacements, with FK506 being the most recent candidate. However, without understanding the mechanisms by which cyclosporin (or FK506) functions at the intracellular level, developing improved immunosuppressants represents an extremely difficult research effort with a limited likelihood of success.

Thus, there exists a significant need to understand the functional basis of T cell activation involving NF-AT, particularly with regard to the mechanism by which these immunosuppressants such as CsA and FK506 inhibit transcription of the early activation genes. With such knowledge, improved assays for screening drug candidates would be feasible, which could in turn dramatically enhance the search process. Modulation of the immune system, especially modulation of T cell activation, also may be effected by directly altering the amount or activity of NF-AT. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for modulating the immune response and for screening for modulators of the immune response. These methods utilize polynucleotide sequences encoding NF-$AT_c$ recombinant proteins and complementary polynucleotides which are substantially identical to NF-$AT_c$ polynucleotide sequences.

In one aspect of the invention, NF-$AT_c$ polypeptides and compositions thereof are provided. NF-$AT_c$ polypeptides comprise polypeptide sequences which are substantially identical to a sequence shown in FIG. 1 or a cognate NF-AT$_c$ gene sequence.

Nucleic acid sequences encoding NF-AT$_c$ are provided. The characteristics of the cloned sequences are given, including the nucleotide and predicted amino acid sequence in FIG. 1. Polynucleotides comprising these sequences can serve as templates for the recombinant expression of quantities of NF-AT$_c$ polypeptides, such as human NF-AT$_c$ and murine NF-AT$_c$. Polynucleotides comprising these sequences can also serve as probes for nucleic acid hybridization to detect the transcription and mRNA abundance of NF-AT$_c$ MRNA in individual lymphocytes (or other cell types) by in situ hybridization, and in specific lymphocyte populations by Northern blot analysis and/or by in situ hybridization (Alwine et al. (1977) *Proc. Natl. Acad. Sci. U.S.A.* 74: 5350) and/or PCR amplification and/or LCR detection. Such recombinant polypeptides and nucleic acid hybridization probes have utility for in vitro screening methods for immunomodulatory agents and for diagnosis and treatment of pathological conditions and genetic diseases, such as transplant rejection reactions, T cell-mediated immune responses, lymphocytic leukemias (e.g., T cell leukemia or lymphoma) wherein NF-AT activity contributes to disease processes, autoimmune disease, arthritis, and the like.

In one embodiment, candidate immunomodulatory agents are identified by their ability to block the binding of a NF-AT$_c$ polypeptide to other components of NF-AT (e.g., AP-1) and/or to block the binding of NF-AT to DNA having an NF-AT recognition site. The DNA preferably includes one or more NF-AT binding sites at which a NF-AT protein complex specifically binds. One means for detecting binding of a NF-AT protein comrpising NF-AT$_c$ to DNA is to immobilize the DNA, such as by covalent or noncovalent chemical linkage to a solid support, and to contact the immobilized DNA with a NF-AT protein complex comprising a NF-AT$_c$ polypeptide that has been labeled with a detectable marker (e.g., by incorporation of radiolabeled amino acid). Such contacting is typically performed in aqueous conditions which permit binding of a NF-AT protein to a target DNA containing a NF-AT binding sequence. Binding of the labeled NF-AT to the immobilized DNA is measured by determining the extent to which the labeled NF-AT$_c$ polypeptide is immobilized as a result of a specific binding interaction. Such specific binding may be reversible, or may be optionally irreversible if a cross-linking agent is added in appropriate experimental conditions.

In one aspect, candidate immunomodulatory agents are identified as being agents capable of inhibiting (or enhancing) intermolecular binding between NF-AT$_c$ and other polypeptides which comprise a NF-AT complex (e.g., AP-1, JunB, etc.). The invention provides methods and compositions for screening libraires of agents for the capacity to interfere with binding of NF-AT$_c$ to other NF-AT polypeptide species under aqueous binding conditions. Typically, at least either NF-AT$_c$ and/or another NF-AT polypeptide species is labeled with a detectable label and intermolecular binding between NF-AT$_c$ and other NF-AT polypeptide species is detected by the amount of labeled species captured in NF-AT complexes and the like.

The invention also provides antisense polynucleotides complementary to NF-AT$_c$ sequences which are employed to inhibit transcription and/or translation of the cognate mRNA species and thereby effect a reduction in the amount of the respective NF-AT$_c$ protein in a cell (e.g., a T lymphocyte of a patient). Such antisense polynucleotides can function as immunomodulatory drugs by inhibiting the formation of NF-AT protein required for T cell activation.

In a variation of the invention, polynucleotides of the invention are employed for diagnosis of pathological conditions or genetic disease that involve T cell neoplasms or T cell hyperfunction of hypofunction, and more specifically conditions and diseases that involve alterations in the structure or abundance of NF-AT$_c$ polypeptide, NF-AT$_c$ polynucleotide sequence, or structure of the NF-AT$_c$ gene or flanking region(s).

The invention also provides antibodies which bind to NF-AT$_c$ with an affinity of about at least $1 \times 10^7$ $M^{-1}$ and which lack specific high affinity binding for other proteins present in activated T cells. Such antibodies can be used as diagnostic reagents to identify T cells (e.g., activatable T cells) in a cellular sample from a patient (e.g., a lymphocyte sample, a solid tissue biopsy) as being cells which contain an increased amount of NF-AT$_c$ protein determined by standardization of the assay to be diagnostic for activated T cells. Frequently, anti-NF-AT$_c$ antibodies are included as diagnostic reagents for immunohistopathology staining of cellular samples in situ. Additionally, anti-NF-AT$_c$ antibodies may be used therapeutically by targeted delivery to T cells (e.g., by cationization or by liposome/immunoliposome delivery).

The invention also provides NF-AT$_c$ polynucleotide probes for diagnosis of neoplasia or immune status by detection of NF-AT$_c$ mRNA in cells explanted from a patient, or detection of a pathognomonic NF-AT$_c$ allele (e.g., by RFLP or allele-specific PCR analysis). A pathognomonic NF-AT$_c$ allele is an allele which is statistically correlated with the presence of a predetermined disease or propensity to develop a disease. Typically, the detection will be by in situ hybridization using a labeled (e.g., $^{32}$P, $^{35}$S, $^{14}$C, $^{3}$H, fluorescent, biotinylated, digoxigeninylated) NF-AT$_c$ polynucleotide, although Northern blotting, dot blotting, or solution hybridization on bulk RNA or poly $A^+$ RNA isolated from a cell sample may be used, as may PCR amplification using NF-AT$_c$-specific primers. Cells which contain an increased amount of NF-AT$_c$ mRNA as compared to standard control values for cells or cell types other than activated T cells or activatable T cells will be thereby identified as activated T cells or activatable T cells. Similarly, the detection of pathognomonic rearrangements or amplification of the NF-AT$_c$ locus or closely linked loci in a cell sample will identify the presence of a pathological condition or a predisposition to developing a pathological condition (e.g., cancer, genetic disease).

The present invention also provides a method for diagnosing T cell hypofunction of hyperfunction in a human patient, wherein a diagnostic assay (e.g., immunohistochemical staining of fixed lymphocytic cells by an antibody that specifically binds human NF-AT$_c$) is used to determine if a predetermined pathognomonic concentration of NF-AT$_c$ protein or NF-AT$_c$ mRNA is present in a biological sample from a human patient; if the assay indicates the presence of NF-AT$_c$ protein or NF-AT$_c$ mRNA at or above such predetermined pathognomonic concentration, the patient is diagnosed as having T cell hyperfunction or hypofunction condition, or transplant rejection and the like.

All publications and patent applications herein are incorporated by reference to the same extent as if each individual publication or patent application was specifically and individually indicated to be incorporated by reference.

BRIEF DESCRIPTION OF THE FIGURES

FIGS. 1A and 1E (SEQ ID NOS: 45–46) the nucleotide sequence of the human NF-AT$_c$ cDNA and the deduced amino acid sequence. Nucleotide sequence and complete predicted amino acid sequence of $NF\text{-}AT_c$ from human T lymphocytes. Bovine peptides (sequences not completely conserved) identified in the predicted human sequence are underlined. The cDNA ends in a canonical polyadenylation signal and a poly A tail.

FIG. 5A: Ribonuclease protection for human $NF\text{-}AT_c$ with RNA from Jurkat cells (lanes 1–6) or Hela cells (lane 7). The expected specific ribonuclease-resistant fragment is 304 nucleotides (arrow). Hela cells were non-stimulated. Jurkat cells were either non-stimulated or stimulated with 20 ng/ml PMA and 2 uM ionomycin for 3 hours, plus or minus 100 ng/ml CsA added at the indicated times after stimulation. FIG. 5B: RNA from the following human cells: KJ (preB cell ALL), JD-1 (B cell lineage ALL), K562 (erythroleukemia cell line), CML (bone marrow cells from a patient with a myeloid leukemia), human muscle tissue, Hep G2 (liver cell line), HPB ALL (T cell line, nonstimulated or stimulated with 2 ug/mi PHA and 50 ng/ml PMA for 30 minutes), and Hela cells analyzed by ribonuclease protection. A longer exposure of this gel indicates that the K562 cell line contains a small amount of $NF\text{-}AT_c$ transcript. FIG. 5C: $NF\text{-}AT_c$ (upper panel) and $NF\text{-}AT_p$ (lower panel) mRNA expression in mouse tissues and a skin tumor derived from NF-AT-Tag transgenic mice (Verweij et al. (1990)*J. Biol. Chem* 265: 15788–15795). Cells were either non-stimulated or stimulated with 20 ng/ml PMA and 2 uM ionomycin for 3 hours. RNA was measured by quantiative ribonuclease protection using murine cDNA probes. The predicted size of the fragment homologous to the probe is indicated by the arrows.

FIG. 6A: Cos cells and Jurkat cells were transfected with reporter constructs for NF-AT or HNF-1 (β28). Co-transfected expression vectors for $NF\text{-}AT_c$ (+NF-AT) or HNF-1α(+HNF-1) were included where indicated, otherwise empty pBJ5 vector was included. Cells were stimulated as indicated: PMA, P+I (PMA plus ionomycin). FIG. 6B: Cos cells were transfected with IL-2 luciferase and with expression vectors as in FIG. A. Stimulations were as in a. Data in FIGS. 6A and 6B are expressed as fold induction of luciferase activity over nonstimulated value with empty pBJ5 vector. Bars represent mean and range of 2–3 independent transfections. FIG. 6C: Expression of $NF\text{-}AT_c$ in Cos cells gives rise to specific DNA binding activity. Gel mobility shifts using nuclear extracts from Cos cells transfected with pBJ5 (lanes 1 and 3), with $NF\text{-}AT_c$ (lanes 2 and 4–7), from non-transfected Jurkat cells (lanes 8–11) or using cytosols from pBJ5- or $NF\text{-}AT_c$-transfected Cos cells (lanes 12–13, 15–16) combined with Hela nuclear extract (lanes 15–16). Lane 14, Hela nuclear extract alone. Labeled AP-1 (lanes 1–2) or NF-AT (lanes 3–16) probes and cold competitor oligonucleotides are indicated. Arrows indicate specific AP-1 and NF-AT complexes. FIG. 6D: Antisera induced supershift of NF-AT. NF-AT and AP-1 gel mobility shifts using nuclear extracts from stimulated Jurkat cells or murine thymocytes. Either no antisera, preimmune, or one of two different immune antisera was included as indicated. Arrows indicate specific NF-AT or AP1 complexes or super-shifted NF-AT complexes (*).

DEFINITIONS

Figure 2:
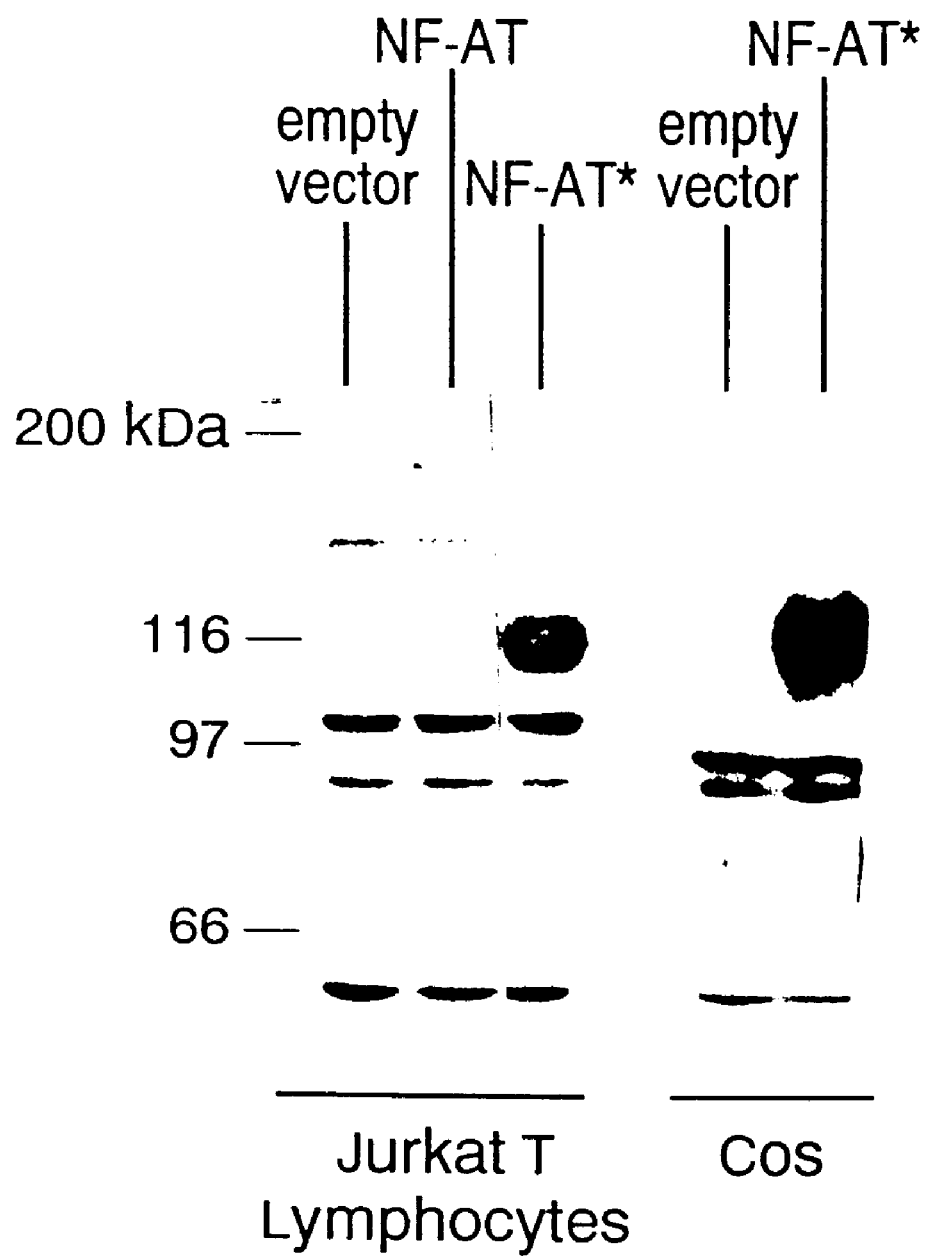
FIG. 2 shows the expression of $NF\text{-}AT_c$ protein in T cells (Jurkat) and non-T cells (Cos).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the PNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length cDNA or gene sequence given in a sequence listing, such as a polynucleotide sequence of FIG. 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis. or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human NF-AT$_c$ polynucleotide sequence shown in FIG. 1 or the full-length murine or bovine NF-AT$_c$ cDNA sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "NF-AT$_c$ native protein" and "full-length NF-AT$_c$ protein" as used herein refers to a a naturally-occurring NF-AT$_c$ polypeptide corresponding to the deduced amino acid sequence shown in FIG. 1 or corresponding to the deduced amino acid sequence of a cognate full-length cDNA. Also for example, a native NF-AT$_c$ protein present in naturally-occurring lymphocytes which express the NF-AT$_c$ gene are considered full-length NF-AT$_c$ proteins.

The term "NF-AT$_c$ fragment" as used herein refers to a polypeptide that has an amino-terminal and/or carboxy-terminal deletion, but where the remaining amino acid sequence is identical to the corresponding positions in the NF-AT$_c$ sequence deduced from a full-length cDNA sequence (e.g., the cDNA sequence shown in FIG. 1). NF-AT$_c$ fragments typically are at least 14 amino acids long, preferably at least 20 amino acids long, usually at least 50 amino acids long or longer.

The term "NF-AT$_c$ analog" as used herein refers to polypeptides which are comprised of a segment of at least 25 amino acids that has substantial identity to a portion of the deduced amino acid sequence shown in FIG. 1, and which has at least one of the following properties: (1) binding to other NF-AT proteins (e.g., AP-1) under suitable binding conditions, or (2) ability to localize to the nucleus upon T cell activation. Typically, NF-AT$_c$ analog polypeptides comprise a conservative amino acid substitution (or addition or deletion) with respect to the naturally-occurring sequence. NF-AT$_c$ analogs typically are at least 20 amino acids long, preferably at least 50 amino acids long or longer, most usually being as long as full-length naturally-occurring NF-AT$_c$ (e.g., as shown in FIG. 1). Some NF-AT$_c$ analogs may lack biological activity but may still be employed for various uses, such as for raising antibodies to NF-AT$_c$ epitopes, as an immunological reagent to detect and/or purify α-NF-AT$_c$ antibodies by affinity chromatography, or as a competitive or noncompetitive agonist, antagonist, or partial agonist of native NF-AT$_c$ protein function.

The term "NF-AT$_c$ polypeptide" is used herein as a generic term to refer to native protein, fragments, or analogs of NF-AT$_c$. Hence, native NF-AT$_c$, fragments of NF-AT$_c$, and analcas of NF-AT$_c$ are species of the NF-AT$_c$ polypeptide genus. Preferred NF-AT$_c$ polypeptides include: the human full-length NF-AT$_c$ protein comprising the polypeptide sequence shown in FIG. 1, or polypeptides consisting essentially of a sequence shown in Table II.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate murine gene to the human NF-AT$_c$ gene is the murine gene which encodes an expressed protein which has the greatest degree of sequence identity to the human NF-AT$_c$ protein and which exhibits an expression pattern similar to that of the human NF-AT$_c$ (e.g., expressed in T lineage cells). Preferred cognate NF-AT$_c$ genes are: rat NF-AT$_c$, rabbit NF-AT., canine NF-AT$_c$, nonhuman primate NF-AT$_c$, porcine NF-AT$_c$, bovine NF-ATR, and hamster NF-AT$_c$.

The term "INF-AT$_c$-dependent gene" is used herein to refer to genes which: (1) have a NF-AT binding site (a site which can be specifically footprinted by NF-AT under suitable binding conditions) within about 10 kilobases of the first coding sequence of said gene, and (2) manifest an altered rate of transcription, either increased or decreased, from a major or minor transcriptional start site for said gene, wherein such alteration in transcriptional rate correlates with the presence of NF-AT$_c$ polypeptide in NF-AT complexes, such as in an activated T cell.

The term "altered ability to modulate" is used herein to refer to the capacity to either enhance transcription or inhibit transcription of a gene; such enhancement or inhibition may be contingent on the occurrence of a specific event, such as T cell stimulation. This alteration will be manifest as an inhibition of the transcriptional enhancement of the IL-2 gene that normally ensues following T cell stimulation. The altered ability to modulate transcriptional enhancement or inhibition may affect the inducible transcription of a gene, such as in the just-cited IL-2 example, or may effect the basal level transcription of a gene, or both.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as immunomodulatory agents (e.g., immunosuppressants) by inclusion in screening assays described hereinbelow.

The term "candidate imunomodulatory agent" is used herein to refer to an agent which is identified by one or more screening method(s) of the invention as a putative immuomodulatory agent. Some candidate immunomodulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the terms "pathognomonic concentration", "pathognomonic amount", and "pathognomonic staining pattern" refer to a concentration, amount, or localization pattern, respectively, of a NF-AT$_c$ protein or mRNA in a sample, that indicates the presence of a hypofunctional or hyperfunctional T cell condition or a predisposition to developing a disease, such as graft rejection. A pathognomonic amount is an amount of a NF-AT$_c$ protein or NF-AT$_c$ mRNA in a cell or cellular sample that falls outside the range of normal clinical values that is established by prospective and/or retrospective statistical clinical studies. Generally, an individual having a neoplastic disease (e.g., lymphocytic leukemia) or T cell-mediated immune response will exhibit an amount of NF-AT$_c$ protein or mRNA in a cell or tissue sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

DETAILED DESCRIPTION

Generally, the nomenclature used hereafter and the laboratory procedures in cell culture, molecular genetics, and nucleic acid chemistry and hybridization described below are those well known and commonly employed in the art. Standard as techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Commonly assigned application U.S. Ser. No. 07/749,385 filed Aug. 22, 1991 is incorporated herein by reference.

Cloning of NF-AT$_c$ Polynucleotides

Genomic or cDNA clones encoding NF-AT$_c$ may be isolated from clone libraries (e.g., available from Clontech, Palo Alto, Calif.) using hybridization probes designed on the basis of the nucleotide sequences shown in FIG. 1 and using conventional hybridization screening methods (e.g., Benton WD and Davis RW (1977) *Science* 196: 180; Goodspeed et al. (1989) *Gene* 76: 1; Dunn et al. (1989) *J. Biol. Chem.* 264: 13057). Where a cDNA clone is desired, clone libraries containing cDNA derived from T cell mRNA is preferred. Alternatively, synthetic polynucleotide sequences corresponding to all or part of the sequences shown in FIG. 1 may be constructed by chemical synthesis of oligonucleotides.

Additionally, polymerase chain reaction (PCR) using primers based on the sequence data disclosed in FIG. 1 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used. In an embodiment, a polynucleotide comprising the 2742 nucleotide-long sequence of FIG. 1 can be used. Alternative polynucleotides encoding the 716 amino acid sequence of FIG. 1 can also be readily constructed by those of skill in the art by using the degeneracy of the genetic code. Polynucleotides encoding amino acids 418 to 710 of the NF-AT$_c$ sequence of FIG. 1 can also be constructed by those of skill in the art.

It is apparent to one of skill in the art that nucleotide substitutions, deletions, and additions may be incorporated into the polynucleotides of the invention. Nucleotide sequence variation may result from sequence polymorphisms of various NF-AT$_c$ alleles, minor sequencing errors, and the like. However, such nucleotide substitutions, deletions, and additions should not substantially disrupt the ability of the polynucleotide to hybridize to one of the polynucleotide sequences shown in FIG. 1 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1), wherein the probe preferentially hybridizes to the specific target such that, for example, a single band corresponding to NF-AT$_c$ mRNA (or bands corresponding to multiple alternative splicing products of the NF-AT$_c$ gene) can be identified on a Northern blot of RNA prepared from a suitable cell source (e.g., a T cell expressing NF-AT$_c$). Polynucleotides of the invention and recombinantly produced NF-AT$_c$, and fragments or analogs thereof, may be prepared on the basis of the sequence data provided in FIG. 1 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif. which are incorporated herein by reference.

NF-AT$_c$ polynucleotides may be short oligonucleotides (e.g., 25–100 bases long), such as for use as hybridization probes and PCR (or LCR) primers. NF-AT$_c$ polynucleotide sequences may also comprise part of a larger polynucleotide (e.g., a cloning vector comprising a NF-AT$_c$ clone) and may be fused, by polynucleotide linkage, in frame with another polynucleotide sequence encoding a different protein (e.g., glutathione S-transferase or β-galactosidase) for encoding expression of a fusion protein. Typically, NF-AT$_c$ polynucleotides comprise at least 25 consecutive nucleotides which are substantially identical to a naturally-occurring NF-AT$_c$ sequence (e.g., FIG. 1), more usually NF-AT$_c$ polynucleotides comprise at least 50 to 100 consecutive nucleotides which are substantially identical to a naturally-occurring NF-AT$_c$ sequence. However, it will be recognized by those of skill that the minimum length of a NF-AT$_c$ polynucleotide required for specific hybridization to a NF-AT$_c$ target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

For example but not limitation, suitable hybridization probes for detecting and/or quantifying the presence of NF-AT$_c$ mRNA in a sample generally comprise at least one, preferably at least two, and more preferably all of the following human NF-AT$_c$ sequences shown in Table I, or their complements:

Table I Selected Human NF-AT$_c$ PolYnucleotide Sequences

5'-TTC CTC CGG GGC GCG CGG CGT GAG CCC GGG GCG AGG-3'(SEQ ID NO:1);
5'-CAG CGC GGG GCG GCC ACT TCT CCT GTG CCT CCG CCC GCT GCT-3'(SEQ ID NO:2);
5'-GCC GCG CGG ATG CCA AGC ACC AGC TTT CCA GTC CCT TCC AAG-3'(SEQ ID NO:3);
5'-CCA ACG TCA GCC CCG CCC TGC CGC TCC CCA CGG CGC ACT CCA-3'(SEQ ID NO:4);
5'-TTC AGA CCT CCA CAC CGG GCA TCA TCC CGC CGG CGG-3'(SEQ ID NO:5);
5'-GCC ACA CCA GGC CTG ATG GGG CCC CTG CCC TGG AGA GTC CTC-3'(SEQ ID NO:6);
5'-AGT CTG CCC AGC CTG GAG GCC TAC AGA GAC CCC TCG TGC CTG-3'(SEQ ID NO:7);
5'-GTG TCT CCC AAG ACC ACG GAC CCC GAG GAG GGC TTT CCC-3'(SEQ ID NO:8);
5'-AGC TGG CTG GGT GCC CGC TCC TCC AGA CCC GCG TCC CCT TGC-3'(SEQ ID NO:9);
5'-TAC AGC CTC AAC GGC CGG CAG CCG CCC TAC TCA CCC CAC CAC-3'(SEQ ID NO:10);
5'-GAC CAC CGA CAG CAG CCT GGA CCT GGG AGA TGG CGT CCC TGT-3'(SEQ ID NO:11);
5'-CCT GGG CAG CCC CCC GCC CCC GGC CGA CTT CGC GCC CGA AGA-3'(SEQ ID NO:12);
5'-GCT CCC CTA CCA GTG GCG AAG CCC AAG CCC CTG TCC CCT ACG-3'(SEQ ID NO:13);
5'-CTT CGG ATT GAG GTG CAG CCC AAG TCC CAC CAC CGA GCC CAC-3'(SEQ ID NO:14);
5'-CAT GGC TAC TTG GAG AAT GAG CCG CTG ATG CTG CAG CTT TTC-3'(SEQ ID NO:15);
5'-AAG ACC GTG TCC ACC ACC AGC CAC GAG GCT ATC CTC TCC AAC-3'(SEQ ID NO:16);
5'-TCA GCT CAG GAG CTG CCT CTG GTG GAG AAG CAG AGC ACG GAC-3'(SEQ ID NO:17);
5'-AAC GCC ATC TTT CTA ACC GTA AGC CGT GAA CAT GAG CGC G-3'(SEQ ID NO:18);
5'-AGA AAC GAC GTC GCC GTA AAG CAG CGT GGC GTG TGG CA-3'(SEQ ID NO:19); and
5'-GCA TAC TCA GAT AGT CAC GGT TAT TTT GCT TCT TGC GAA TG-3'(SEQ ID NO:20).

Also for example but not limitation, the following pair of PCR primers (amplimers) may be used to amplify murine or human NF-AT$_c$ sequences (e.g., by reverse transcriptase initiated PCR of RNA from NF-AT$_c$ expressing cells):
(forward)
5'-AGGGCGCGGGCACCGGGGCGCGGGCAGGGC CGGAG-3'(SEQ ID NO:21)
(reverse)
5'-GCAAGAAGCAAAATAACCGTGACTATCTGAG TATGC-3'(SEQ ID NO:22)
If desired, PCR amplimers for amplifying substantially full-length cDNA copies may be selected at the discretion of the practitioner. Similarly, amplimers to amplify single NF-AT$_c$ exons or portions of the NF-AT$_c$ gene (murine or human) may be selected.

Each of these sequences may be used as hybridization probes or PCR amplimers to detect the presence of NF-AT$_c$ mRNA, for example to diagnose a disease characterized by the presence of an elevated NF-AT$_c$ mRNA level in lymphocytes, or to perform tissue typing (i.e., identify tissues characterized by the expression of NF-AT$_c$ mRNA), and the like. The sequences may also be used for detecting genomic NF-AT$_c$ gene sequences in a DNA sample, such as for forensic DNA analysis (e.g., by RFLP analysis, PCR product length(s) distribution, etc.) or for diagnosis of diseases characterized by amplification and/or rearrangements of the NF-AT$_c$ gene.

Production of NF-AT$_c$ Polypeptides

The nucleotide and amino acid sequences shown in FIG. 1 enable those of skill in the art to produce polypeptides corresponding to all or part of the full-length human NF-AT$_c$ polypeptide sequence. Such polypeptides may be produced in prokaryotic or eukaryotic host cells by expression of polynucleotides encoding NF-AT$_c$, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of NF-AT$_c$ may be prepared by those of skill in the art. Preferred amino- and carboxy-termini of fragments or analogs of NF-AT$_c$ occur near boundaries of functional domains. For example, but not for limitation, such functional domains include: (1) domains conferring the property of binding to other NF-AT components (e.g., AP-1), (2) domains conferring the property of nuclear localization in stimulated T lymphocytes, and (3) domains conferring the property of enhancing activation of T cells when expressed at sufficient levels in such cells. Additionally, such functional domains might include: (1) domains conferring the property of binding to RNA polymerase species, (2) domains having the capacity to directly alter local chromatin structure, which may comprise catalytic activities (e.g., topoisomerases, endonucleases) and/or which may comprise structural features (e.g., zinc fingers, histone-binding moieties), and (3) domains which may interact with accessory proteins and/or transcription factors.

One method by which structural and functional domains may be identified is by comparison of the nucleotide and/or amino acid sequence data shown in FIG. 1 to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous *(Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the NF-AT$_c$ sequences of the invention. One example of a domain is the rel similarity region from amino acid 418 to amino acid 710 of the NF-AT$_c$ polypeptide sequence of FIG. 1.

Additionally, computerized comparison of sequences shown in FIG. 1 to existing sequence databases can identify sequence motifs and structural conformations found in other proteins or coding sequences that indicate similar domains of the NF-AT$_c$ protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a NF-AT$_c$ sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in NF-AT$_c$ polypeptides (Brunak et al. (1991) *J. Mol. Biol.* 220: 49, which is incorporated herein by reference). For example, the 13-residue repeat motifs -SPRASVTEESWLG-(SEQ ID NO:23) and -SPRVSVTDDSWLG-(SEQ ID NO:24) are examples of structurally related domains.

Fragments or analogs comprising substantially one or more functional domain may be fused to heterologous polypeptide sequences, wherein the resultant fusion protein exhibits the functional property(ies) conferred by the NF-AT$_c$ fragment. Alternatively, NF-AT$_c$ polypeptides wherein one or more functional domain have been deleted will exhibit a loss of the property normally conferred by the missing fragment.

By way of example and not limitation, the domain conferring the property of nuclear localization and/or interaction with AP-1 may be fused to β-galactosidase to produce a fusion protein that is localized to the nucleus and which can enzymatically convert a chromogenic substrate to a chromophore.

Although one class of preferred embodiments are fragments having amino- and/or carboxy-termini corresponding to amino acid positions near functional domains borders, alternative NF-AT$_c$ fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of NF-AT$_c$ can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native NF-AT$_c$ protein. However, NF-AT$_c$ analogs must comprise a segment of 25 amino acids that has substantial similarity to a portion of the amino acid sequence shown in FIG. 1, respectively, and which has at least one of the requisite functional properties enumerated in the Definitions (supra). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with calcineurin or phophorylation or dephosphorylation thereby. NF-AT$_c$ analogs include various muteins of a NF-AT$_c$ sequence other than the naturally-occurring peptide sequence. For example, single or multiple amino acid substitutions (preferably conservative amino acid substitutions) may be made in the naturally-occurring NF-AT$_c$ sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W.H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Native NF-AT$_c$ proteins, fragments thereof, or analogs thereof can be used as reagents in DNA binding assays and/or in vitro transcription assays for identifying agents that interfere with NF-AT function, said agents are thereby identified as candidate drugs which may be used, for example, to block T cell activation or treat T cell lymphocytic leukemias. Typically, in vitro DNA binding assays that measure binding of NF-AT to DNA employ double-stranded DNA that contains an array of one or more NF-AT recognition sites (as defined by specific footprinting of native NF-AT protein). The DNA is typically linked to a solid substrate by any of various means known to those of skill in the art; such linkage may be noncovalent (e.g., binding to a highly charged surface such as Nylon 66) or may be by covalent bonding (e.g., typically by chemical linkage involving a nitrogen position in a nucleotide base, such as diazotization). NF-AT$_c$ polypeptides are typically labeled by incorporation of a radiolabeled amino acid. The labeled NF-AT$_c$ polypeptide, usually reconstituted with an NF-AT nuclear component (e.g., AP-1 activity) to form an NF-AT complex, is contacted with the immobilized DNA under aqueous conditions that permit specific binding in control binding reactions with a binding affinity of about $1 \times 10^6$ M$^{-1}$ or greater (e.g., 10–250 mM NaCl or KCl and 5–100 mM Tris HCl pH 5–9, usually pH 6–8), generally including Zn$^{+2}$ and/or Mn$^{+2}$ and/or Mg$^{+2}$ in the nanomolar to micromolar range (1 nM to 999 μM). Specificity of binding is typically established by adding unlabeled competitor at various concentrations selected at the discretion of the practitioner. Examples of unlabeled protein competitors include, but are not limited to, the following: unlabeled NF-AT$_c$ polypeptide, bovine serum albumin, and nuclear protein extracts. Binding reactions wherein one or more agents are added are performed in parallel with a control binding reaction that does not include an agent. Agents which inhibit the specific binding of NF-AT$_c$ polypeptides to DNA, as compared to a control reaction, are identified as candidate immunomodulatory drugs. Also, agents which prevent transcriptional modulation by NF-AT in vitro are thereby identified as candidate immunomodulatory drugs.

In addition to NF-AT$_c$ polypeptides consisting only of naturally-occuring amino acids, NF-AT$_c$ peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human NF-AT$_c$, but have one or more peptide linkages optionally replaced by a linkage selected from the group consisting of: —CH$_2$NH—, —CH$_2$S—, —CH$_2$—CH$_2$, —CH=CH— (cis and trans), —COCH$_2$—, —CH(OH)CH$_2$—, and —CH$_2$SO—, by methods known in the art and further described in the following references: Spatola, A.F. in "Chemistry and Biochemistry of Amino Acids, Peptides, and Proteins," B. Weinstein, eds., Marcel Dekker, New York, p. 267 (1983); Szatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pent Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R. G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic. Peptidomimetics of NF-AT$_c$ may be used as competitive or noncompetitive agonists or antagonists of NF-AT$_c$ function. For example, a NF-AT$_c$ peptidomimetic administered to a stimulated T cell containing NF-AT$_c$ and may compete with the naturally-occurring NF-AT$_c$ and reduce NF-AT activity. Alternatively, an NF-AT$_c$ peptidomimetic administerd to a T cell lacking NF-AT$_c$ may induce T cell activation or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

The amino acid sequences of NF-AT$_c$ polypeptides identified herein will enable those of skill in the art to produce polypeptides corresponding to NF-AT$_c$ peptide sequences and sequence variants thereof. Such polypeptides may be produced in prokaryotic or eukaryotic host cells by expression of polynucleotides encoding a NF-AT$_c$ peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91: 501; Chaiken I. M. (1981) CRC Crit. Rev. Biochem. 11: 255; Kaiser et al.(1989) Science 243: 187; Merrifield, B. (1986) Science 232: 342; Kent, S. B. H. (1988) Ann. Rev. Biochem. 57: 957; and Offord, R. E. (1980) Semisynthetic Proteins, Wiley Publishing, which are incorporated herein by reference).

Production and Applications of α-NF-AT$_c$ Antibodies

Native NF-AT$_c$ proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see Antibodies: A Laboratory Manual, (1988) E. Harlow and D. Lane, Cold Spring Harbor Laboratory, Cold Spring Harbor, N.Y., which is incorporated herein by reference.

For example but not for limitation, a recombinantly produced fragment of human NF-AT$_c$ can be injected into a rat along with an adjuvant following immunization protocols known to those of skill in the art so as to generate an immune response. Typically, approximately at least 1–50 µg of a NF-AT$_c$ fragment or analog is used for the initial immunization, depending upon the length of the polypeptide. Alternatively or in combination with a recombinantly produced NF-AT$_c$ polypeptide, a chemically synthesized peptide having a NF-AT$_c$ sequence (e.g., peptides exemplified in Table II, infra) may be used as an immunogen to raise antibodies which bind a NF-AT$_c$ protein, such as the native human NF-AT$_c$ polypeptide having the sequence shown essentially in FIG. 1 or the native human NF-AT$_c$ polypeptide isoform. Immunoglobulins which bind the recombinant fragment with a binding affinity of at least $1 \times 10^7 \text{ M}^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced NF-AT$_c$ polypeptide (or chemically synthesized NF-AT$_c$ polypeptide) with an affinity of at least $1\times10^6$ M$^{-1}$. Animals other than mice and rats may be used to raise antibodies; for example, goats, rabbits, sheep, and chickens may also be employed to raise antibodies reactive with a NF-AT$_c$ protein. Transgenic mice having the capacity to produce substantially human antibodies also may be immunized and used for a source of α-NF-ATC antiserum and/or for making monoclonal-secreting hybridomas.

Bacteriophage antibody display libraries may also be screened for binding to a NF-AT$_c$ polypeptide, such as a full-length human NF-AT$_c$ protein, a NF-AT$_c$ fragment (e.g., a peptide having a sequence shown in Table II, infra), or a fusion protein comprising a NF-AT$_c$ polypeptide sequence of at least 14 contiguous amino acids as shown in FIG. 1 or a polypeptide sequence of Table II (infra). Combinatorial libraries of antibodies have been generated in bacteriophage lambda expression systems which may be screened as bacteriophage plagues or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnoloy* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a NF-AT$_c$ polypeptide that is immobilized (e.g., by covalent linkage to a chromatography resin to enrich for reactive phage by affinity chromatography) and/or labeled (e.g., to screen plaque or colony lifts).

NF-AT$_c$ polypeptides which are useful as immunogens, for diagnostic detection of α-NF-ATC antibodies in a sample, for diagnosic detection and quantitation of NF-AT$_c$ protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least 95 percent (w/w) purity, being substantially free of other proteins of humans, mice, or other contaminants. Preferred immunogens comprise at least one NF-AT$_c$ polypeptide sequence shown in Table II, either as a discrete peptide or as part of a fusion polypeptide (e.g., with a β-galactosidase or glutathione S-transferase sequence). NF-AT$_c$ immunogens comprise at least one, typically several of such immunogenic epitopes.

For some applications of these antibodies, such as identifying immunocrossreactive proteins, the desired antiserum or monoclonal antibody(ies) is/are not monospecific. In these instances, it may be preferable to use a synthetic or recombinant fragment of NF-AT$_c$ as an antigen rather than using the entire native protein. More specifically, where the object is to identify immunocrossreactive polypeptides that comprise a particular structural moiety, such as a DNA-binding domain, it is preferable to use as an antigen a fragment corresponding to part or all of a commensurate structural domain in the NF-AT$_c$ protein. Production of recombinant or synthetic fragments having such defined amino- and carboxy-termini is provided by the NF-AT$_c$ sequences shown in FIG. 1.

If an antiserum is raised to a NF-AT$_c$ fusion polypeptide, such as a fusion protein comprising a NF-AT$_c$ immunogenic epitope fused to β-galactosidase or glutathione S-transferase, the antiserum is preferably preadsorbed with the non-NF-AT$_c$ fusion partner (e.g, β-galactosidase or glutathione S-transferase) to deplete the antiserum of antibodies that react (i.e., specifically bind to) the non-NF-AT$_c$ portion of the fusion protein that serves as the immunogen. Monoclonal or polyclonal antibodies which bind to the human and/or murine NF-AT$_c$ protein can be used to detect the presence of human or murine NF-AT$_c$ polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured NF-AT$_c$ epitopes and may be identified visually or by other optical means with a labeled second antibody or labeled *Staphylococcus aureus* protein A by methods known in the art. Frequently, denatured NF-AT$_c$ will be used as the target antigen so that more epitopes may be available for binding.

TABLE II

Selected Human NF-AT$_c$ Antigen Peptides

-NAIFLTVSREHERVGC-(SEQ ID NO:25);
-LHGYLENEPLMLQLFIGT-(SEQ ID NO:26);
-PSTSPRASVTEESWLG-(SEQ ID NO:27);
-GPAPRAGGTMKSAEEEHYG-(SEQ ID NO:28);
-ASAGGHPIVQ-(SEQ ID NO:29);
-NTRVRLVFRV-(SEQ ID NO:30);
-AKTDRDLCKPNSLVVEIPPFRN-(SEQ ID NO:31);
-EVQPKSHHRAHYETEGSR-(SEQ ID NO:32);
-SPRVSVTDDSWLGNT-(SEQ ID NO:33);
-SHHRAHYETEGSRGAV-(SEQ ID NO:34);
-LRNSDIELRKGETDIGR-(SEQ ID NO:35);
-TLSLQVASNPIEC-(SEQ ID NO:36).

Such NF-AT$_c$ sequences as shown in Tables II may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred NF-AT$_c$ polypeptide comprises the following amino acids sequences:
-PSTSPRASVTEESWLG-(SEQ ID NO:27);
-SHHRAHYETEGSRGAV-(SEQ ID NO:33);
-SPRVSVTDDSWLGNT-(SEQ ID NO:34);
-NAIFLTVSREHERVGC-(SEQ ID NO:25);
and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. One application of the preferred NF-AT$_c$ polypeptide just recited is as a commercial immunogen to raise α-NF-AT$_c$, antibodies in a suitable animal and/or as a commercial immunodiagnostic reagent for quantitative ELISA (e.g., competitive ELISA) or competitive RIA in conjunction with the anti-NF-AT$_c$, antibodies provided by the invention, such as for calibration of standardization of such immunoassays for staging or diagnosis of NF-AT$_c$-expressing lymphocytic leukemias in humans or cell typing or identification of T cells (such as activated T cells and/or activatable T cells). The preferred NF-AT$_c$ polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent NF-AT$_c$ antigen, comprising at least two NF-AT$_c$ immunogenic epitopes in covalent linkage, usually in peptide linkage. Such polyvalent NF-AT$_c$ antigens typically comprise multiple NF-AT$_c$ antigenic peptides from the same species (e.g., human or mouse), but may comprise a mix of antigenic peptides from NF-AT$_c$ proteins of different species (i.e., an interspecies NF-AT$_c$ polyvalent antigen). Frequently, the spatial order of the antigenic peptide sequences in the primary amino acid sequence of a polyvalent antigen occurs in the same orientation as in the naturally occurring NF-AT$_c$ protein (i.e., a first antigenic peptide sequence that is amino-terminal to a second antigenic peptide sequence in a naturally occurring NF-AT$_c$r protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or psuedorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:

-NAIFLTVSREHERVGC(SEQ ID NO:25)-(aa1)-AKTDRDLCKPNSLVVEIPPFRN(SEQ ID NO:31)-(aa2)-VKASAGGHPIVQL(SEQ ID NO:37)

where (aa1) and (aa2) are peptide spacers of at least one amino acid and less than 1000 amino acids; aal is a peptide sequence selected independently from the aa2 peptide sequence; the length of aal (which may be composed of multiple different amino acids) is independent of the length of aa2 (which may be composed of multiple different amino acids).

Immunogenic NF-AT$_c$ peptides may be used to immunize an animal to raise anti-NF-AT$_c$ antibodies and/or as a source of spleen cells for making a hybridoma library from which to select hybridoma clones which secrete a monoclonal antibody which binds to a NF-AT$_c$ protein with an affinity of $1\times10^7$ M$^{-1}$ or greater, preferably at least $1\times10^8$ M$^{-1}$ to $1\times10^9$ M$^{-1}$. Such immunogenic NF-AT$_c$ peptides can also be used to screen bacteriophage antibody display libraries directly.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel transcription factors or chromatin proteins. Such screening of cDNA expression libraries is well known in the art, and is further described in Young et al., *Proc. Natl. Acad. Sci. U.S.A.* 80:1194–1198 (1983), which is incorporated herein by reference] as well as other published sources. Another use of such antibodies is to identify and/or purify immunocrossreactive proteins that are structurally or evolutionarily related to the native NF-AT$_c$ protein or to the corresponding NF-AT$_c$ fragment (e.g., functional domain; DNA-binding domain) used to generate the antibody. It is believed that such antibodies will find commercial use as such reagents for research applications, just as other antibodies (and biological reagents—such as restriction enzymes and polymerases) are sold commercially.

Various other uses of such antibodies are to diagnose and/or stage leukemias or other immunological disease states, and for therapeutic application (e.g., as cationized antibodies or by targeted liposomal delivery) to treat neoplasia, hyperimmune function, graft rejection, and the like.

An example of an NF-AT$_c$ polypeptide is a polypeptide having the sequence:
MPSTSFPVPSKFPLGPAAAVFGRGETLG-
PAPRAGGTMKSAEEEHYGYASSNVSPAL-
PLPTAHSTLPAPCHNLQTSTPGIIP-
PADHPSGYGAALDGCPAGYFLSSGHTRPDGAPALE
SPRIEITSCLGLYHNNNQFFHDVEVEDV-
LPSSKRSPSTATLSLPSLEAYRDPSCLS-
PASSLSSRSCNSEASSYESNYSYP-
YASPQTSPWQSPCVSPKTTDPEEGFPRGLGACTLLG
SPQHSPSTSPRASVTEESWLGARSSR-
PASPCNKRKYSLNGRQPPYSPHH-
SPTPSPHGSPRVSVTDDSWLGNTTQYTS-
SAIVAAINALTTDSSLDLGDGVPVKSRKTTLEQPPSV
ALKVEPVGEDLGSPPPPADFAPEDYSSFQHIR KGG-
FCDQYLAVPQHPYQWAKPKPLSPTSYMSPTLP
LDWQLPSHSGPYELRIEVQPKSHHRAHYETEGSRG
AVKASAGGHPIVQLHGYLENEPL,
MLQLFIGTADDRLLRPHAFYQVHRITGKTVSTTSHE
AILSNTKVLEIPLLPENSMRAVIDCACILKLRNSDIEL
RKGETDIGRKNTRVRLVFRVHVPQPSGRTLSLQVAS
PIECSQRSAQELPLVEKQSTDSYPVVGGKKMVLSG
HNFLQDSKVIFVEKAPDGHHVWEMEAKTDRDLCK
PNSLVVEIPPFRNQRITSPVHVSFYVCNGKRKRSQY
QRFTYLPANGNAIFLTVSREHERVGCFF(SEQ ID NO:38)

NF-AT$_c$ Polynucleotides

Disclosure of the full coding sequence for human NF-AT$_c$ shown in FIG. 1 makes possible the construction of isolated polynucleotides that can direct the expression of NF-AT$_c$, fragments thereof, or analogs thereof. Further, the sequences in FIG. 1 make possible the construction of nucleic acid hybridization probes and PCR primers that can be used to detect RNA and DNA sequences encoding NF-AT$_c$.

Polynucleotides encoding full-length NF-AT$_c$ or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a NF-AT$_c$ polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred NF-AT$_c$ polynucleotide encodes a NF-AT$_c$ polypeptide that comprises at least one of the following amino acids sequences:
-NAIFLTVSREHERVGC-(SEQ ID NO:25);
-LHGYLENEPLMLQLFIGT-(SEQ ID NO:26);
-PSTSPRASVTEESWLG-(SEQ ID NO:27);
-GPAPRAGGTMKSAEEEHYG-(SEQ ID NO:28);
-ASAGGHPIVQ-(SEQ ID NO:29);
-NTRVRLVFRV-(SEQ ID NO:30);
-AKTDRDLCKPNSLVVEIPPFRN-(SEQ ID NO:31);
-EVQPKSHHRAHYETEGSR-(SEQ ID NO:32);
-SPRVSVTDDSWLGNT-(SEQ ID NO:33);
-SHHRAHYETEGSRGAV-(SEQ ID NO:34);
-LRISDIELRKGETDIGR-(SEQ ID NO:35);
-TLSLQVASNPIEC-(SEQ ID NO:36);.

The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Thus, isolated polynucleotides typically less than approximately 10,000 nucleotides in length and comprising sequences encoding each of the following amino acid sequences:
-NAIFLTVSREHERVGC-(SEQ ID NO:25);
-LHGYLENEPLMLQLFIGT-(SEQ ID NO:26);
-PSTSPRASVTEESWLG-(SEQ ID NO:27);
-GPAPRAGGTMKSAEEEHYG-(SEQ ID NO:28);
-ASAGGHPIVQ-(SEQ ID NO:29);
-NTRVRLVFRV-(SEQ ID NO:30);
-AKTDRDLCKPNSLVVEIPPFRN-(SEQ ID NO:31);
-EVQPKSHHRAHYETEGSR-(SEQ ID NO:32);
-SPRVSVTDDSWLGNT-(SEQ ID NO:33);
-SHHRAHYETEGSRGAV-(SEQ ID NO:34);
-LRNSDIELRKGETDIGR-(SEQ ID NO:35);
-TLSLQVASNPIEC-(SEQ ID NO:36).
are provided and may be used for, among other uses, the expression of a NF-AT$_c$ polypeptide which can be used as an immunogen, immunological reagent, and the like. Such polynucleotides typically comprise an operably linked promoter for driving expression in a suitable prokaryotic or eukaryotic host cell. One exemplification of such a polynucleotide is the human NF-AT$_c$ cDNA sequence of FIG. 1 cloned in operable linkage to the mammalian expression vector pSRα, many alternative embodiments will be apparent to those of skill in the art, including the use of alternative expression vectors (e.g., pBC12BI and p91023(B); Hanahan J (1983) *J. Mol. Biol.* 166: 577; Cullen et al. (1985) *J. Virol.* 53: 515; Lomedico PT (1982) *Proc. Natl. Acad. Sci. (U.S.A.)* 79: 5798; Morinaga et al. (1984) *Bio/Technology* 2: 636).

Additionally, where expression of a polypeptide is not desired, polynucleotides of this invention need not encode a functional protein. Polynuclectides of this invention may serve as hybridization probes and/or PCR primers (amplimers) and/or LCR oligomers for detecting NF-AT$_c$ RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the NF-AT$_c$ sequence is retained.

Specific hybridization is defined hereinbefore, and can be roughly summarized as the formation of hybrids between a polynucleotide of the invention (which may include substitutions, deletions, and/or additions) and a specific target polynucleotide such as human NF-AT$_c$ mRNA so that a single band is identified corresponding to each NF-AT$_c$ isoform on a Northern blot of RNA prepared from T cells (i.e., hybridization and washing conditions can be established that permit detection of discrete NF-AT$_c$ mRNA band(s)). Thus, those of ordinary skill in the art can prepare polynucleotides of the invention, which may include substantial additions, deletions, substitutions, or transpositions of nucleotide sequence as compared to sequences shown in FIG. 1 and determine whether specific hybridization is a property of the polynucleotide by performing a Northern blot using RNA prepared from a T lymphocyte cell line which expresses NF-AT$_c$ mRNA and/or by hybridization to a NF-AT$_c$ DNA clone (cDNA or genomic clone).

Specific amplification is defined as the ability of a set of PCR amplimers, when used together in a PCR reaction with a NF-AT$_c$ polynucleotide, to produce substantially a single major amplification product which corresponds to a NF-AT$_c$ gene sequence or mRNA sequence. Generally, human genomic DNA or mRNA from NF-AT$_c$ expressing human cells (e.g., Jurkat cell line) is used as the template DNA sample for the PCR reaction. PCR amplimers that exhibit specific amplification are suitable for quantitative determination of NF-AT$_c$ mRNA by quantitative PCR amplification. NF-AT$_c$ allele-specific amplification products, although having sequence and/or length polymorphisms, are considered to constitute a single amplification product for purposes of this definition.

Generally, hybridization probes comprise approximately at least 25 consecutive nucleotides of a sequence shown in FIG. 1 (for human and murine NF-AT$_c$ detection, respectively), preferably the hybridization probes contain at least 50 consecutive nucleotides of a sequence shown in FIG. 1, and more preferably comprise at least 100 consecutive nucleotides of a sequence shown in FIG. 1. PCR amplimers typically comprise approximately 25 to 50 consecutive nucleotides of a sequence shown in FIG. 1, and usually consist essentially of approximately 25 to 50 consecutive nucleotides of a sequence shown in FIG. 1 with additional nucleotides, if present, generally being at the 5' end so as not to interfere with polymerase-mediated chain extension. PCR amplimer design and hybridization probe selection are well within the scope of discretion of practioners of ordinary skill in the art.

Methods Relating to Genetic Disease

In one preferred embodiment of the invention, hybridization probes that specifically identify the NF-AT$_c$ gene may be used in methods for diagnosing genetic disease. For example, but not for limitation, the genetic disease thus diagnosed may involve a lesion in the relevant NF-AT$_c$ structural or regulatory sequences, or may involve a lesion in a genetic locus closely linked to the NF-AT$_c$ locus and which can be identified by restriction fragment length polymorphism or DNA sequence polymorphism at the linked NF-AT$_c$ locus. In a further preferred embodiment, NF-AT$_c$ gene probes are used to diagnose or identify genetic disease involving predisposition to immunological disease, wherein the amount or functionality of endogenous NF-AT$_c$ is sufficient for the individual to exhibit an increased probability of developing an immune disease, particularly an immune deficiency, arthritis, or autoimmune disease.

Antisense Polynucleotides

Additional embodiments directed to modulation of T cell activation include methods that employ specific antisense polynucleotides complementary to all or part of the sequences shown in FIG. 1. Such complementary antisense polynucleotides may include nucleotide substitutions, additions, deletions, or transpositions, so long as specific hybridization to the relevant target sequence corresponding to FIG. 1 is retained as a functional property of the polynucleotide. Complementary antisense polynucleotides include soluble antisense RNA or DNA oligonucleotides which can hybridize specifically to NF-AT$_c$ mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., W091/11535; U.S. Ser. Nos. 07/530,165; W091/09865; W091/04753; W090/13641; and EP 386563, each of which is incorporated herein by reference). The antisense polynucleotides therefore inhibit production of NF-AT$_c$ polypeptides. Since NF-AT$_c$ protein expression is associated with T lymphocyte activation, antisense polynucleotides that prevent transcription and/or translation of mRNA corresponding to NF-AT$_c$ polypeptides may inhibit T cell activation and/or reverse the the activated phenotype of T cells. Compositions containing a therapeutically effective dosage of NF-AT$_c$ antisense polynucleotides may be administered for treatment of immune diseases, including lymphocytic leukemias, and for inhibition of transplant rejection reactions, if desired. Antisense polynucleotides of various lengths may be produced, although such antisense polynucleotides typically comprise a sequence of about at least 25 consecutive nucleotides which are substantially identical to a naturally-occurring NF-AT$_c$ polynucleotide sequence, and typically which are identical to a sequence shown in FIG. 1.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Isolation of the Cognate Human NF-AT$_c$ Gene

The human homolog of the NF-AT$_c$ cDNA is identified and isolated by screening a human genomic clone library, such as a human genomic library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 1. Typically, hybridization and washing conditions are performed at high stringency according to conventional hybridization procedures. Positive clones are isolated and sequenced. For illustration and not for limitation, a full-length polynucleotide corresponding to the sequence of FIG. 1 may be labeled and used as a hybridization probe to isolate genomic clones from a human or murine genomic clone libary in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100 200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C. for about 6–36 hours. Prehybridization conditions are essentially identical except that probe is not included and incubation time is typically reduced. Washing conditions are typically 1–3× SSC, 0.1–1% SDS, 50–70° C. with hange of wash solution at about 5–30 minutes.

Nonhuman NF-AT$_c$ cDNAs and genomic clones (i.e., cognate nonhuman NF-AT$_c$ genes) can be analogously isolated from various nonhuman cDNA and genomic clone libraries available in the art (e.g., Clontech, Palo Alto, Calif.) by using probes based on the sequences shown in FIG. 1, with hybridization and washing conditions typically being less stringent than for isolation of human NF-AT$_c$ clones.

Polynucleotides comprising sequences of approximately at least 30–50 nucleotides, preferably at least 100 nucleotides, corresponding to or complementary to the nucleotide sequences shown in FIG. 1 can serve as PCR primers and/or hybridization probes for identifying and isolating germline genes corresponding to NF-AT$_c$. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 1. Human genomic libraries are publicly available or may be constructed de novo from human DNA.

Genomic clones of NF-AT$_c$, particularly of the murine cognate NF-AT$_c$ gene, may be used to construct homologous targeting constructs for generating cells and transgenic nonhuman animals having at least one functionally disrupted NF-AT$_c$ allele, preferably homozygous for knocked out NF-AT$_c$ alleles. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated NF-AT$_c$ allele. Such mice may be sold commercially as research animals for investigation of immune system development, neoplasia, T cell activation, signal transduction, drug sreening, and other uses.

Chimeric targeted mice are derived according to Hogan, et al., *Manipulating the Mouse Embryo: A Laboratory*

Manual, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a NF-AT$_c$ cDNA or genomic gene copy may be used to construct transgenes for expressing NF-AT$_c$ polypeptides at high levels and/or under the transcriptional control of transcription control sequences which do not naturally occur adjacent to the NF-AT$_c$ gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a NF-AT$_c$-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential immunomodulatory agents, as overexpression of NF-AT$_c$ or inappropriate expression of NF-AT$_c$ may result in a hyperimmune state or enhance graft rejection reactions.

Identification and Isolation of Proteins That Bind NF-AT$_c$

Proteins that bind to NF-AT$_c$ and/or a NFAT-DNA complex are potentially important transcriptional regulatory proteins. Such proteins may be targets for novel Immunomodulatory agents. These proteins are referred to herein as accessory proteins. Accessory proteins may be isolated by various methods known in the art.

One preferred method of isolating accessory proteins is by contacting a NF-AT$_c$ polypeptide to an antibody that binds the NF-AT$_c$ polypeptide, and isolating resultant immune complexes. These immune complexes may contain accessory proteins bound to the NF-AT$_c$ polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to NF-AT$_c$ and/or a NFAT-DNA complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a NF-AT$_c$ polypeptide may be constructed by oligonucleotide synthesis, placed in an expression vector, and expressed in a host cell.

Putative accessory proteins that bind NF-AT$_c$ and/or NFAT-DNA complex in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a NF-AT$_c$ polypeptide. For a general discussion of crosslinking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the NF-AT$_c$ polypeptide. Isolation of crosslinked complexes that include a NF-AT$_c$ polypeptide is preferably accomplished by binding an antibody that binds a NF-AT$_c$ polypeptide with an affinity of at least $1 \times 10^7$ M$^{-1}$ to a population of crosslinked complexes and recovering only those complexes that bind to the antibody with an affinity of at least $1 \times 10^7$ M$^{-1}$. Polypeptides that are crosslinked to a NF-AT$_c$ polypeptide are identified as accessory proteins.

Screening assays can be developed for identifying candidate immunomodulatory agents as being agents which inhibit binding of NF-AT$_c$ to an accessory protein (e.g. AP-1) under suitable binding conditions.

Expression of NF-AT$_c$ Poly-entides

The nucleic acid sequences of the present invention capable of ultimately expressing the desired NF-AT$_c$ polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.c., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, New York, N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986) *Immunol. Rev.* 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a NF-AT$_c$ polypeptide) can be transferred into the host cell by well-known methods, which vary depending on the type of cellular host. For example, CaCl transfection is commonly utilized for prokaryotic cells, whereas CaPO$_4$ treatment or electroporation may be used for other cellular hosts. (See, generally, Maniatis, et al., *Molecular Cloning: A Laboratory Manual*, Cold Spring Harbor Press, (1982), which is incorporated herein by reference). Usually, vectors are episomes and are maintained extrachromosomally.

Expression of recombinant NF-AT$_c$ protein in cells, particularly cells of the lymphopoietic lineage, may be used to identify and isolate genes that are transcriptionally modulated, either positively or negatively, by the presence of NF-AT$_c$, protein. Such genes are typically initially identified as cDNA clones isolated from subtractive cDNA libraries, wherein RNA isolated from cells expressing recombinant NF-AT$_c$ and RNA isolated from control cells (i.e., not expressing recombinant NF-AT$_c$) are used to generate the subtractive libraries and screening probes. In such a manner, NF-AT$_c$-dependent genes may be isolated. NFAT-dependent genes (or their regulatory sequences operably linked to a reporter gene) may be used as a component of an in vitro transcription assay employing a NF-AT$_c$ polypeptide as a necessary component for efficient transcription; such transcription assays may be used to screen for agents which inhibit NF-AT$_c$-dependent gene transcription and are thereby identified as candidate immunomodulatory agents.

Methods for Forensic Identification

The NF-AT$_c$ polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the NF-AT$_c$ gene region. On the basis of the NF-AT$_c$ gene structure, the individual from which the sample originated will be identified with respect to his/her NF-AT$_c$ genotype. The NF-AT$_c$ genotype may be used alone or in conjuction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BanHI, SalI, NotI, AccI, ApaI, BglII, XbaI, PstI) under suitable reaction conditions (e.g., see New England Biolabs 1992 catalog). Corresponding digestion products from each individual are loaded separately on an electrophoretic gel (typically agarose), electrophoresed, blotted to a membrane by Southern blotting, and hybridized with a labeled NF-AT$_c$ probe (e.g., a full-length human NF-AT$_c$ cDNA sequence of FIG. 1). Restriction fragments (bands) which are polymorphic among members of the population are used as a basis to discriminate NF-AT$_c$ genotypes and thereby classify individuals on the basis of their NF-AT$_c$ genotype.

Similar categorization of NF-AT$_c$ genotypes may be performed by sequencing PCR amplification products from a population of individuals and using sequence polymorphisms to identify alleles (genotypes), and thereby identify or classify individuals.

Yeast Two-Hybrid Screening Assays

Yeast two-hybrid systems may be used to screen a mammalian (typically human) cDNA expression library, wherein cDNA is fused to a GAL4 DNA binding domain or activator domain, and a NF-AT$_c$ polypeptide sequence is fused to a GAL4 activator domain or DNA binding domain, respectively. Such a yeast two-hybrid system can screen for cDNAs encoding proteins which bind to NF-AT$_c$ sequences. For example, a cDNA library can be produced from mRNA from a human mature T cell line or other suitable cell type. Such a cDNA library cloned in a yeast two-hybrid expression system (Chien et al. (1991) *Proc. Natl. Acad. Sci.* (*U.S.A.*) 88: 9578 or *Cell* 72: 233) can be used to identify cDNAs which encode proteins that interact with NF-AT$_c$ and thereby produce expression of the GAL4-dependent reporter gene. Polypeptides which interact with NF-AT$_c$ can alos be identified by immunoprecipitation of NF-AT$_c$ with antibody and identification of co-precipitating species. Further, polypeptides that bind NF-AT$_c$ can be identified by screening a peptide library (e.g., a bacteriophage peptide display library, a spatially defined VLSIPS peptide array, and the like) with a NF-AT$_c$ polypeptide.

Methods for Rational Drug Desian

NF-AT$_c$ polypeptides, especially those portions which form direct contacts in NF-AT complexes, can be used for rational drug design of candidate NFAT-modulating agents (e.g., antineoplastics and immunomodulators). The substantially purified NF-AT$_c$ and the identification of NF-AT$_c$ as a docking partner for AP-1 activities as provided herein permits production of substantially pure NFAT polypeptide complexes and computational models which can be used for protein X-ray crystallography or other structure analysis methods, such as the DOCK program (Kuntz et al. (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a NF-AT$_c$ polypeptide: AP-1 polypeptide complex. Thus, the present invention may be used to design drugs, including drugs with a capacity to inhibit binding of NF-AT$_c$ to form NFAT.

Particularly preferred variants are structural mimetics of a dominant negative NF-AT$_c$ mutants, such as a polypeptide consisting essentially of amino acids 1–418 of FIG. 1 and substantially lacking amino acids carboxy-terminal to residue 418. Such mimetics of dominant-negative mutant polypeptides can have substantial activity as antagonists or partial agonists of NF-AT activation (and hence T cell activation).

The following examples are offered by way of example and not by way of limitation. Variations and alternate embodiments will be apparent to those of skill in the art.

EXPERIMENTAL EXAMPLES

Overview

We have purified two related proteins encoded by separate genes that represent the preexisting or cytosolic components of NF-AT. Expression of a full length cDNA for one of these proteins, NF-AT$_c$, activates the IL-2 promoter in non-T lymphocytes, while a dominant negative of NF-AT$_c$ specifically blocks activation of the IL-2 promoter in T lymphocytes, indicating that NF-AT$_c$ is required for IL-2 gene expression and is responsible for the restricted expression of IL-2. NF-AT$_c$ RNA expression is largely restricted to lymphoid tissues and is induced upon cell activation. The second protein, NF-AT$_p$, is highly homologous to NF-AT$_c$ over a limited domain, but exhibits wider tissue distribution and is highly expressed in tissues characterized by Ca++-dependent regulation. Together these proteins are members of a new family of DNA binding proteins, which are distantly related to the Dorsal/Rel family (Nolan and Baltimore (1992) *Current Biology. Ltd.* 2: 211–220). Agents i that increase intracellular Ca++ or that activate protein kinase C independently produce alterations in the mobility of NF-AT$_c$, indicating that distinct signaling pathways converge on NP-AT$_c$ to regulate its function.

Since our previous work indicated that the cytosolic component of NF-AT was present at relatively low concentrations in human lymphoid cell lines (Northrop et al. (1993) *J. Biol. Chem.* 268: 2917–2923), we chose to purify NF-AT$_c$ from bovine thymus. Amino acid sequence, obtained from 6 peptides, was used to isolate two overlapping human cDNA clones spanning 2742 nucleotides (FIG. 1). The cDNA encodes a protein of 716 amino acids with a predicted molecular weight of 77,870. An in-frame stop codon upstream from the initiator methionine indicates that the entire NF-AT$_c$ protein is encoded by this cDNA. A unique repeated sequence of 13 residues was also identified. The carboxy-terminal half of NF-AT$_c$ shows limited similarity to the DNA binding and dimerization regions of the Dorsal/Rel family of transcription factors (FIG. 4, for review, Nolan and Baltimore (1992) *Current Biology, Ltd.* 2: 211–220) however, NF-AT$_c$ appears to be the most distantly related member of the group. There are a significant number of amino acid changes resulting in charge reversals between the Rel family members and NF-AT$_c$, suggesting that charge might be conserved at these positions to maintain salt bridges. Six additional peptides obtained from the purified bovine protein are derived from the bovine homolog of NF-AT$_p$, a cDNA fragment of which was reported by McCaffrey et al. (1993) *Science* 262: 750–754). Comparison of NF-AT$_c$ and NF-AT$_p$ reveals that they are products of distinct genes with 73% amino acid identity in the Rel similarity region (FIG. 4), however, there is very little similarity outside this region. A murine cDNA for NF-AT$_c$ was isolated and the predicted protein was found to be 87% identical to human NF-AT$_c$, and distinctly different from murine NF-AT$_p$.

Example 1

Determination of the Nucleotide and Amino Acid Sequence of Human NF-AT$_c$ cDNA

This example represents the isolation and purification of this novel human NF-AT protein, NF-AT$_c$, the determination of the amino acid sequence of its fragments and the isolation and sequencing of the cDNA clone encoding this protein.

The protein was purified from bovine thymus glands obtained from newborn calves. Approximately 20 bovine thymuses were homogenized to make a cytosolic extract which was then subjected sequentially to 1) ammonium sulfate precipitation, 2) sulphopropyl Sepharose chromatography, 3) heparin agarose chromatography, 4) affinity chromatography using a multimerized binding site for NF-AT, with the sequence 5'-ACGCCCAAAGAGGAAAATTTGTTTCATACA-3' (SEQ ID NO:39) coupled to sepharose CL4B, and 5) HPLC on a reverse phase C4 column. The resulting purified protein was subjected to cleavage with LysC/ArgC and fragments isolated by HPLC. The sequences of these individual fragments were then determined by automated Edman degradation. Sequences obtained included: LRNSDIELRKGETDIGR(SEQ ID NO:35) and LRNADIELR (SEQ ID NO:40). Degenerate oligos corresponding to GETDIG (SEQ ID NO:41) (reverse primer) and RNADIE (SEQ ID NO:42) (forward primer) were made. The degenerate oligo PCR primers had the following sequences:

A forward: (A/C)GIAA(C/T)GCIGA(C/T)AT(A/C/T)GA (A/G) (SEQ ID NO:43)

A reverse: ICC(A/G/T)AT(A/G)TCIGT(C/T)TCICC (SEQ ID NO:44)

To isolate the cDNA, oligonucleotide probes were made corresponding to the determined amino acid sequence and used as PCR primers to isolate a 45 base fragment from bovine cDNA prepared from the bovine thymus. The bovine PCR product comprised the nucleotide sequence CTG CGG AAA which encodes -L-R-K-. The same 45 bp fragment can be amplified from human and mouse sources.

This bovine PCR product was then used to screen a cDNA library of the human Jurkat T cell line. Clones were isolated at frequencies of about 1 in 100,000 to 1 in 200,000. A total of five human cDNA clones of various lengths were isolated. Two overlapping clones, one containing the 5' end and one containing the 3' end were ligated together using a unique EcoRI restriction site present in each clone, to produce a full-length cDNA which corresponded in length to the messenger RNA determined by Northern blotting.

The sequence of the NF-AT$_c$ cDNA was determined by the Sanger method and the complete nucletide and predicted amino acid sequence is shown in FIG. 1. The initiator methionine indicated in FIG. 1 was determined by fusing this reading frame to a glutathione transferase gene and transfecting the resultant clone into bacteria. The resultant clone produced a fusion protein of the proper molecular weight, indicating that the reading frame designated with the initiator methionine is indeed the correct reading frame. The position of the stop codon was determined by a similar procedure. In addition, the stop codon corresponds to the reading frame for nine of the determined amino acid sequences.

Figure 4C:
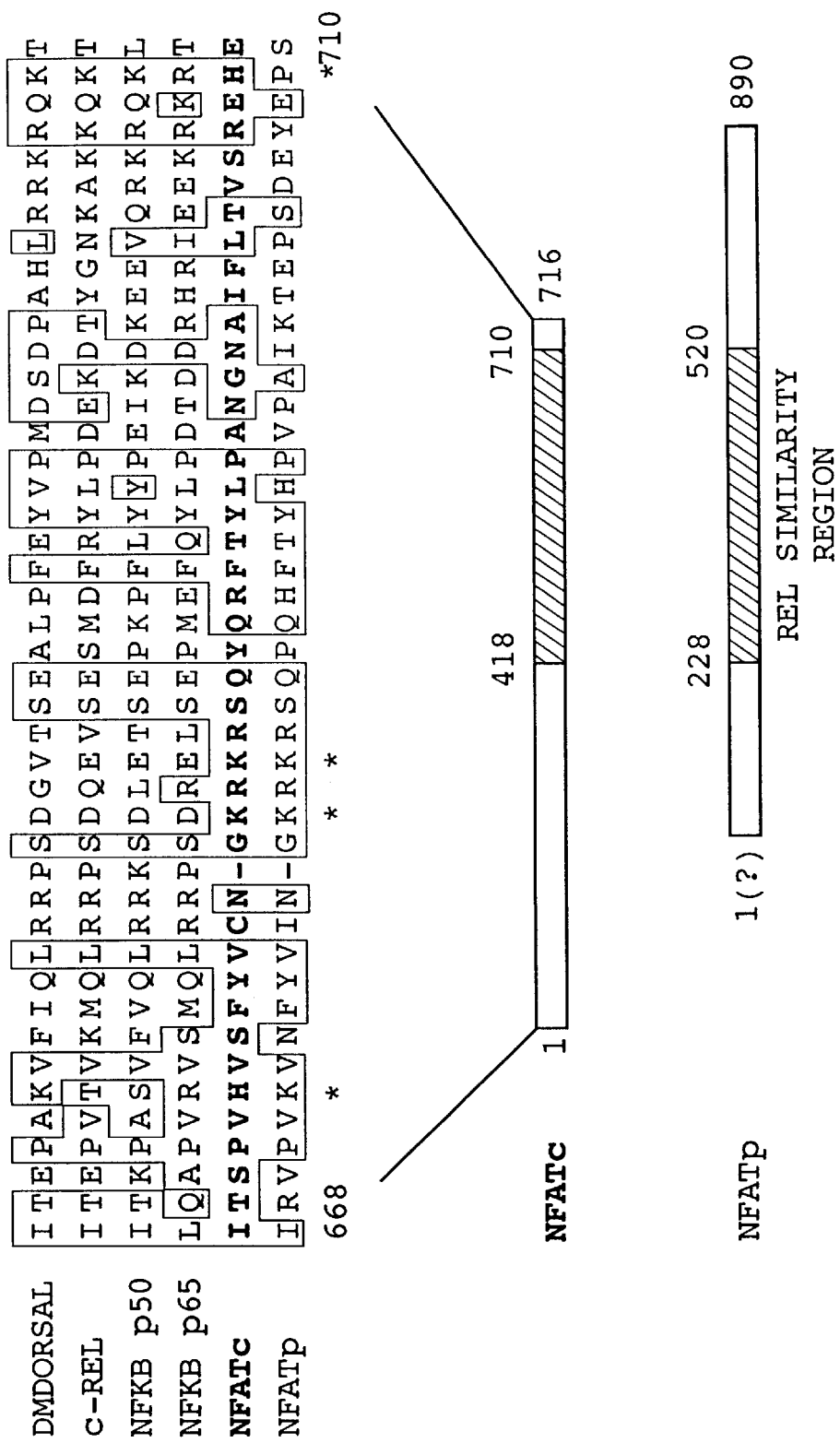
FIG. 4 (SEQ ID NOS: 47–52) shows homology between $NF\text{-}AT_c$, $NF\text{-}AT_p$, and Rel family members. The protein sequences of murine $NF\text{-}AT_p$ and the Rel proteins Dorsal (the Drosophila axis-determining protein), human c-Rel, NF-κB p50, and NF-κB p65 are aligned to the sequence of $NF\text{-}AT_c$. Numbering is with respect to $NF\text{-}AT_c$. Identity to $NF\text{-}AT_c$, open boxes; similarity in known residue function or structure, shaded areas. Stars indicate regions in which $NF\text{-}AT_c$ has: 1) a charge reversal relative to the majority of other Rel proteins, or has 2) replaced a potential salt bridge residue with a histidine or other chelating residue. Lower portion shows a schematic of $NF\text{-}AT_c$ and $NF\text{-}AT_p$.

The total NF-AT$_c$ protein structure was aligned against individual Rel proteins using a MacIntosh shareware program called DOTALIGN utilizing the alignment parameters of the FASTA programs. Significant homology was observed that corresponded to the Rel domains of these proteins. Enhanced amino acid residue alignment was done using ALIGN from the same suite of programs. Alignment of the Rel similarity regions of NF-AT$_c$ and NF-AT$_p$ was done by hand with no insertions necessary, The Miyata alphabet (Miyata et al. (1979) *J. Mol. Evol.* 12: 214–236) was used to determine similar residues. FIG. 4 shows results of such sequence alignments.

Example 2

Expression of NF-AT$_c$ in T and Non-T Cells

The cDNA shown in FIG. 1 was fused to the *Hemophilus influenza* hemaglutinin (HA) 12 amino acid epitope tag in the determined reading frame and operably linked to the SRα promoter in the vector pBJ5 (Lin et al, 1990, Science 249:677–679). The resultant construct was transiently transfected by electroporation into Jurkat human T lymphocytes, and into Cos fibroblast cells. Expression of the epitope-tagged NF-AT$_c$ protein was determined by Western blotting of whole cell extracts prepared from the transfected cells, using an antibody (12CA5, Berkeley Antibody Co., CA) that detects the HA epitope.

FIG. 2 shows that NF-AT$_c$ cDNA construct is able to express a protein of appoximately 120 kDA corresponding precisely in size to that of the purified protein, in both Jurkat T cells and Cos cells (see lanes 3 and 6 labeled NF-AT*. Lane 2 shows as control, NF-AT without the epitope tag which cannot be detected in the Western blot).

Example 3

Transfection of NF-AT$_c$ Activates Transcription in Both Cos and Jurkat Cells

The NF-AT$_c$ cDNA was operably linked to a portion of the SV40 early gene promoter and the HIV transcription regulatory regions in the pBJ vector. This expression vector was co-tranfected into Jurkat and Cos cells with either a) three copies of NF-AT binding site linked to and directing transcription of luciferase (results shown in FIGS. 3A and 3B) the entire IL-2 enhancer/promoter directing transcription of luciferase (results shown in FIG. 3B). Cytosolic extracts were prepared and luciferase assays carried out by standard procedures (de Wet et al, 1987, Mol. Cell. Biol. 7:724–837).

Figure 3A:
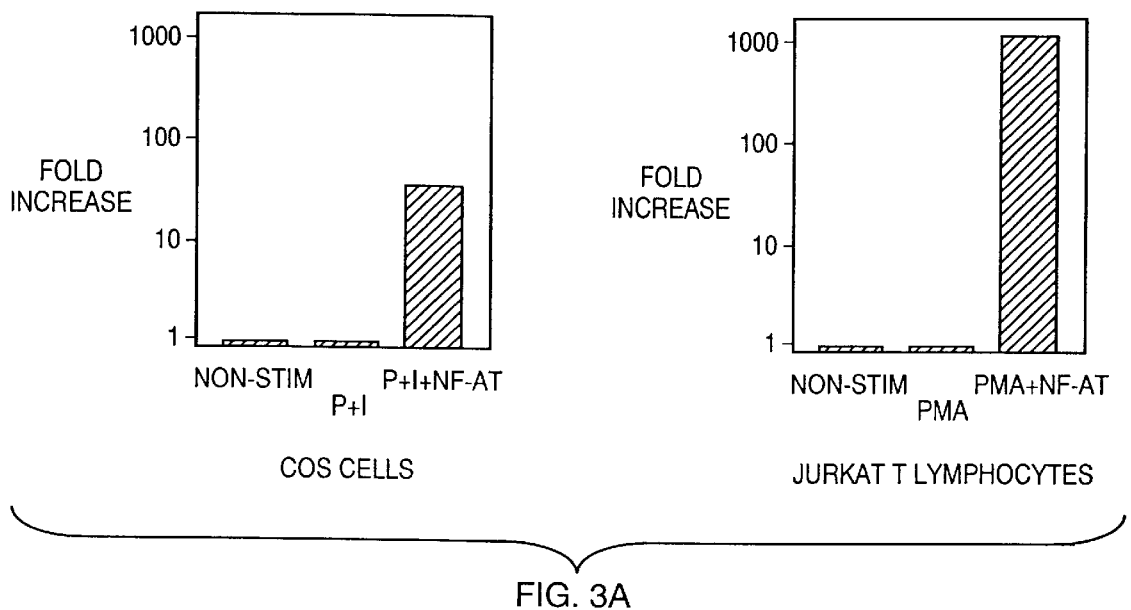
FIGS. 3A and 3B show that the $NF\text{-}AT_c$ cDNA clone encodes a protein that activates transcription from an NF-AT site and is capable of activating the IL-2 promoter in non-T cells.
Figure 3B:
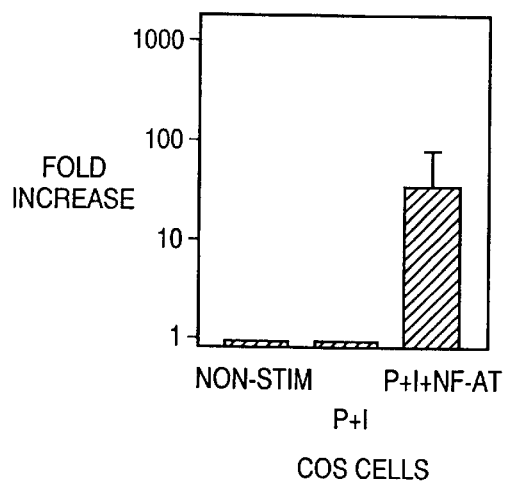

The results demonstrate that in both Cos cells and Jurkat cells, overexpression of the NF-AT$_c$ protein dramatically enhances NF-AT-dependent transcription by 50–1000 fold (see FIG. 3A). In addition, overexpression of the NF-AT$_c$ protein in Cos cells activates the IL-2 promoter, which in the absence of NF-ATC cannot otherwise be activated (see FIG. 3B).

These results indicate that the cDNA clone encodes a functional NF-AT$_c$ protein and that NF-AT$_c$ is the protein which restricts expression of interleukin-2 to T cells.

Example 4

NF-AT$_c$ mRNA and Protein Expression

Figure 5A:
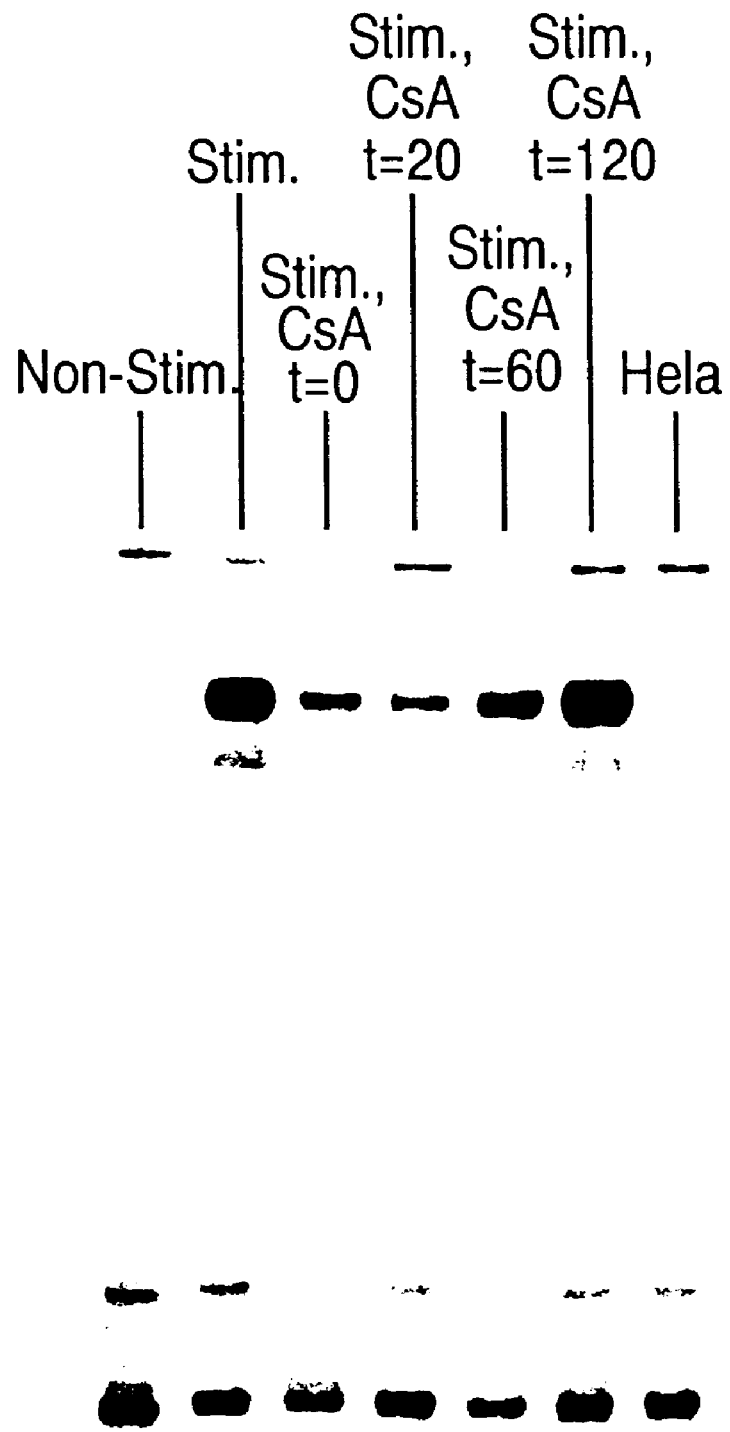
FIGS. 5A–5C.
Figure 5B:
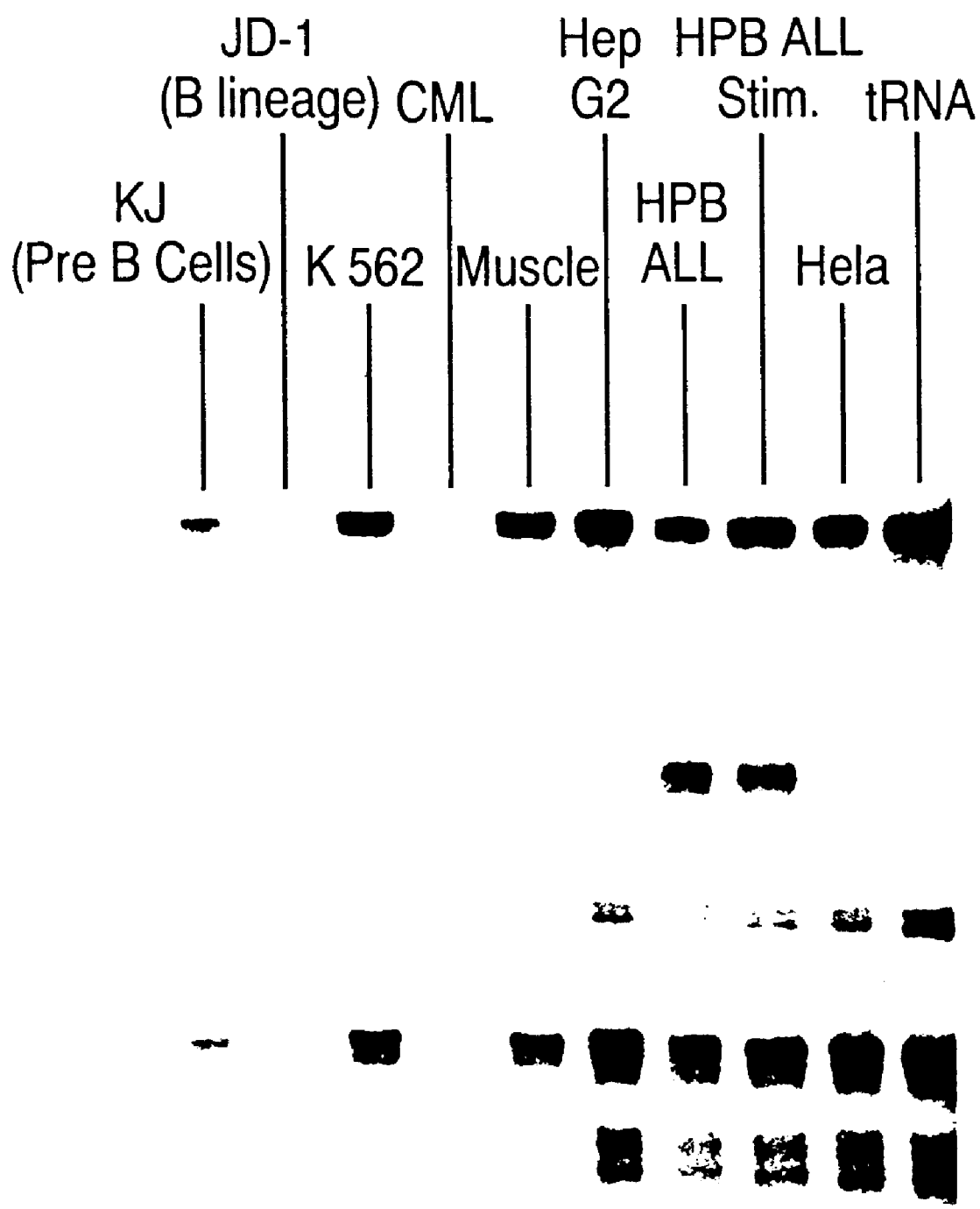
Figure 5C:
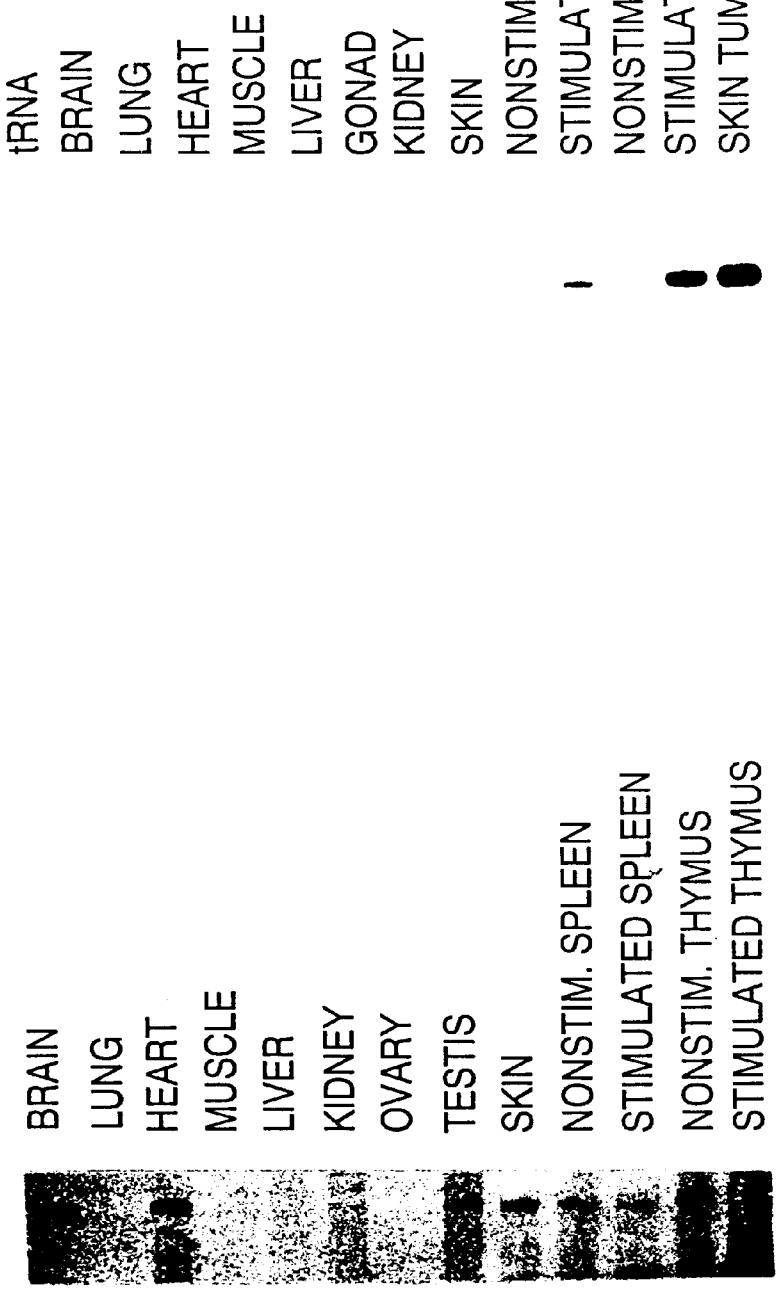
Figure 6A:
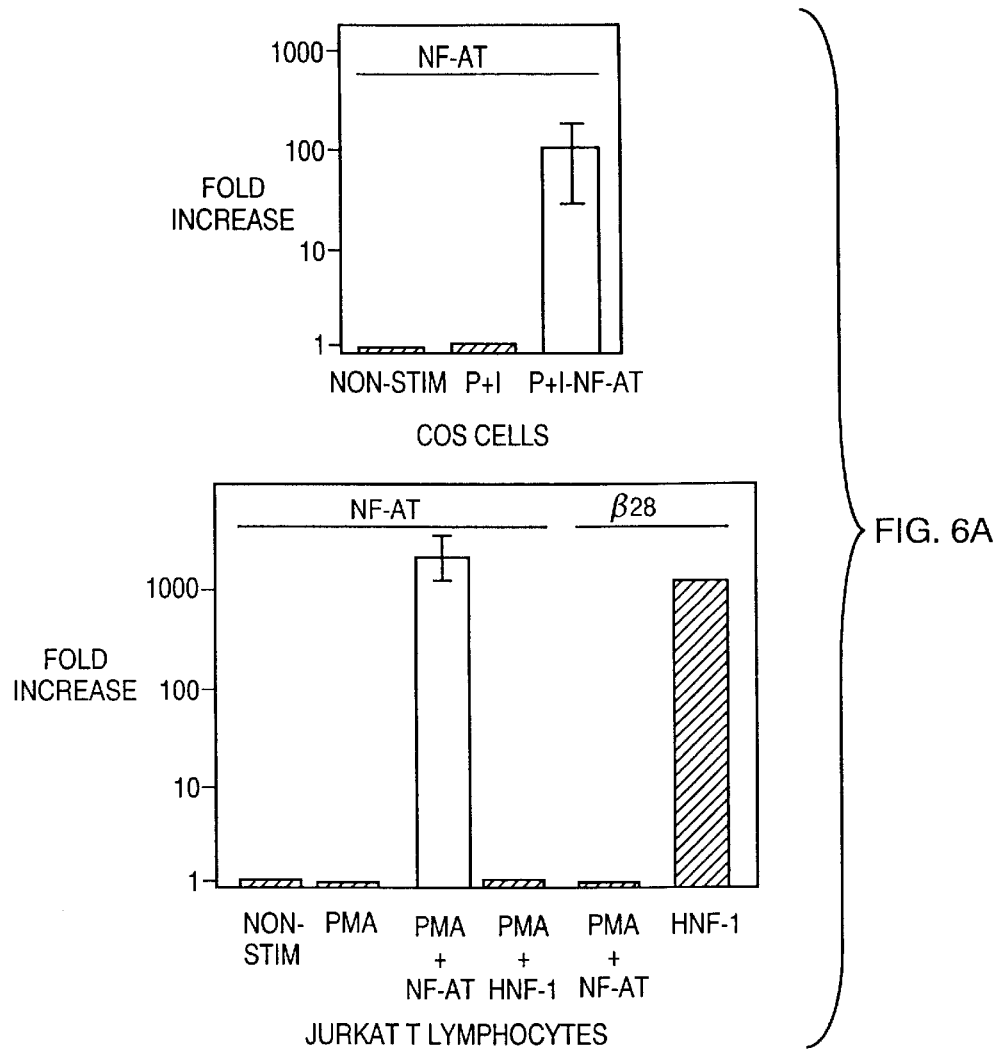
FIGS. 6A–6D.
Figure 6B:
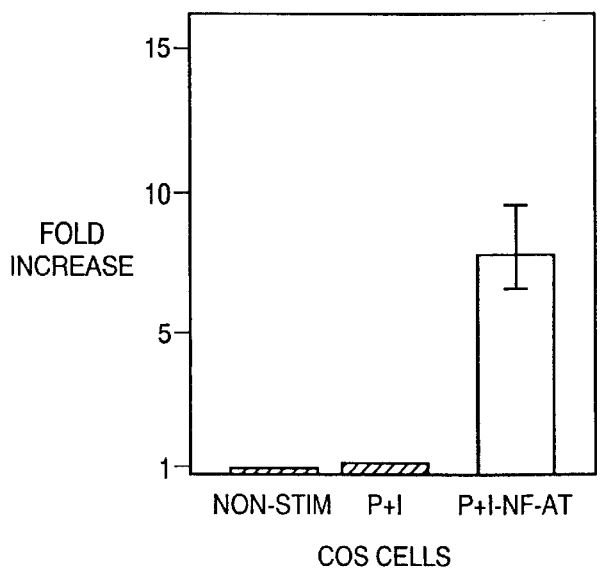
Figure 6C:
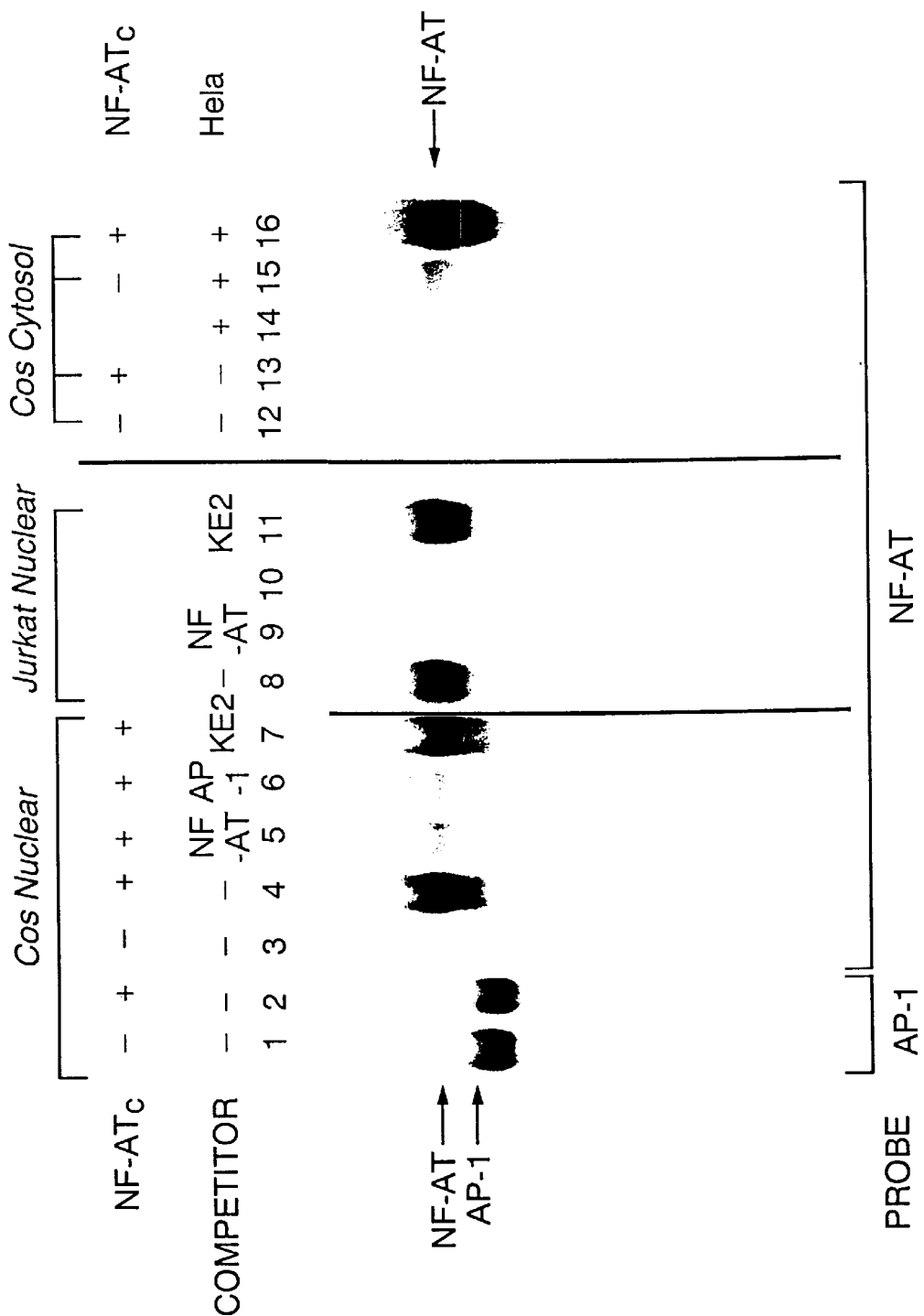
Figure 6D:
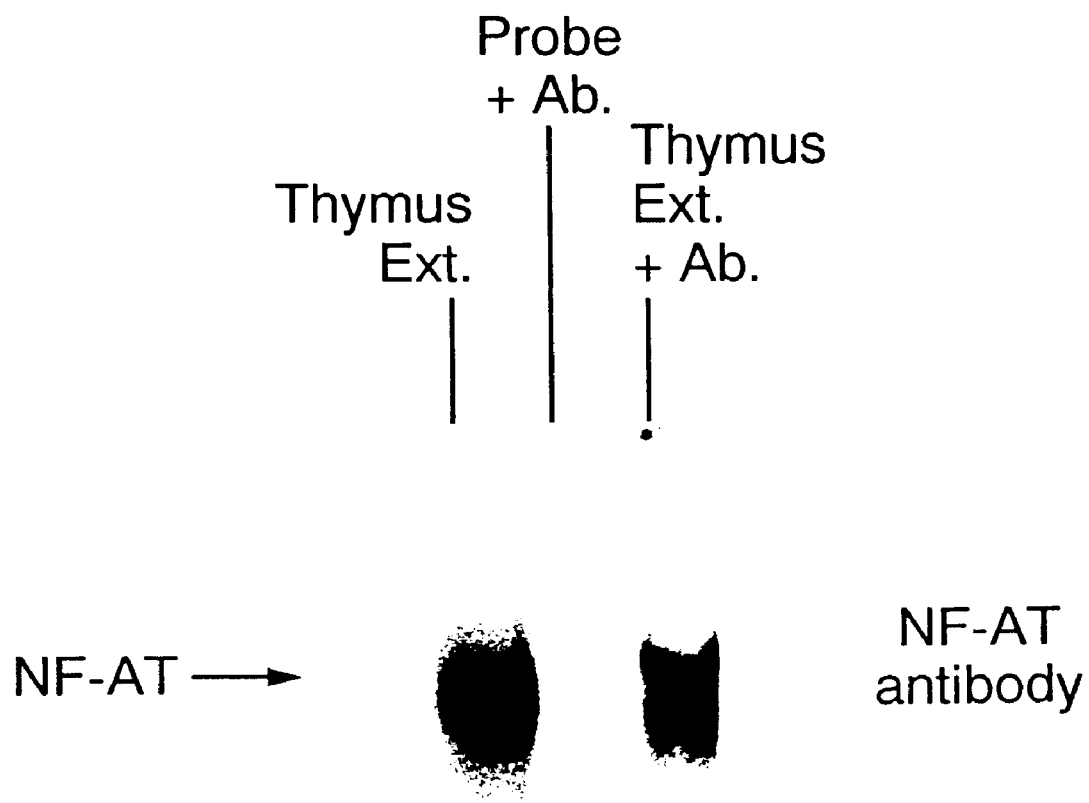

NF-AT$_c$ mRNA is absent in Hela cells (FIG. 5, panel a, lane 7), a cell line incapable of IL-2 or NF-AT-dependent transcription, but is inducible in Jurkat cells (FIG. 5, panel a). This induction is sensitive to cyclosporin A, (CsA), indicating that NF-AT$_c$ may participate in an auto-stimulatory loop as CsA has been shown to block its nuclear association (Flanagan et al. (1991) *Nature* 352: 803–807). Two B cell lines, muscle tissue, Hep G2 cells and myeloid leukemia cells do not express NF-AT$_c$ mRNA (FIG. 5, panel b). These observations are consistent with the observed T cell-restricted pattern of IL-2 transcription and NF-AT activity. Previous studies (Verweij et al. (1990) *J. Biol. Chem* 265: 15788–15795) revealed NF-AT-dependent transcription predominantly in spleen, thymus and skin of transgenic mice expressing an NF-AT-dependent reporter gene. Consistent with these observations, murine NF-AT$_c$ mRNA shows the same pattern of expression (FIG. 5 panel c). Small amounts of NF-AT$_c$ expression are seen in lung and heart, however, this may be due to contamination with circulating T cells. Murine NF-AT$_p$ mRNA, also assayed by quantitative ribonuclease protection, was found to be expressed at approximately equal levels in brain, heart, thymus and spleen (FIG. 5, panel c). In contrast to NF-ATc, NF-AT$_p$ was not inducible by PMA and ionomycin (FIG. 5, panel c).

METHODS. Specific human or mouse NF-AT$_c$ or mouse NF-AT$_p$ cDNA fragments were used as templates for the synthesis of RNA transcripts. Ribonuclease protection was done according to Melton et al. (1984) *Nucl. Acids. Res.* 12: 7035–7056) using 10 µg of total RNA. Splenocytes and thymocytes were isolated and treated as described (Verweij et al. (1990) *J. Biol. Chem* 265: 15788–15795) before isolating RNA, otherwise whole tissue was used.

Example 5

Functional Expression of NF-AT$_c$

NF-AT luciferase and IL-2 luciferase have been described (Northrop et al. (1993) *J. Biol. Chem.* 268: 2917–2923). β28 luciferase was constructed by inserting a trimerized HNF-I recognition site (62 28) in place of the NF-AT recognition sites in NF-AT luciferase. The plasmid pSV2CAT (Gorman et al. (1982) *Mol. Cell. Biol.* 2: 1044–1050) was used as an internal control for transfection efficiency. Cells were transfected with 1.5 ug of luciferase reporter and 3 ug of expression construct as described. After 20 hours of growth, cells were stimulated for 8 hrs. with 20 ng/ml PMA plus or minus 2 uM ionomycin, and harvested for luciferase (de Wet et al. (1987) *Mol. Cell. Biol.* 7: 725–737) and CAT assays (Gorman et al. (1982) *Mol. Cell. Biol.* 2: 1044–1050).

Cos cells were transfected with epitope tagged NF-AT$_c$ as described. Cos cells, Jurkat cells, and murine thymocytes were stimulated for 3hr. with PMA and ionomycin, Hela cells were stimulated for 3hr with PMA alone and nuclear extracts prepared as described (Fiefing et al. (1990) *Genes & Dev.* 4: 1823–1834). cytosols were prepared from non-stimulated Cos cells. Gel mobility shifts were performed as previously described (Flanagan et al. (1991) *Nature* 352: 803–807; Northrop et al. (1993) *J. Biol. Chem.* 268: 2917–2923). Antisera were raised in mice immunized with bacterially expressed glutathione S-transferase fusion proteins using the vector pGEX-3X (Pharmacia) and purified on glutathione agarose. Fusion proteins contained NF-AT$_c$ residues 12 to 143 (immune-1) and 12 to 699 (immune-2).

NF-AT$_c$, expressed in non T cell lines specifically activated transcription from the NF-AT site and the IL-2 promoter, (FIG. 6 panel a (left), and FIG. 6 panel b). In transiently transfected Jurkat cells, overexpression of NF-AT$_c$ activated an NF-AT-dependent promoter but not an HNF-1-dependent promoter (FIG. 6 panel a (right)) or an AP-1-dependent promoter. Transfection of the NF-AT$_c$ cDNA gives rise to DNA binding activity that is indistinguishable from endogenous NF-AT (FIG. 6 panel c, lanes 1–4). Antibody directed against the HA epitope encoded by the transfected cDNA induces a supershift of the NF-AT complex indicating that NF-AT$_c$ participates in this activity. The nuclear NF-AT activity in transfected Cos cells comigrates with, and has the same binding specificity as, the native nuclear complex in T-cells (FIG. 6 panel c, lanes 4–11). Cytosolic extracts from NF-AT$_c$, transfected Cos cells can reconstitute NF-AT DNA binding activity when mixed with Hela nuclear extract (FIG. 6 panel c, lanes 12–16) as do cytosolic extracts from T-cells (Flanagan et al. (1991) Nature 352: 803–807; Northrop et al. (1993) J. Biol. Chem. 268: 2917–2923). Antisera raised against bacterially expressed fragments of NF-AT$_c$ that have no similarity to NF-AT$_p$ are able to induce a supershift of the endogenous NF-AT complex, but not the AP-1 complex, from Jurkat cells or thymocytes (immune-1 and immune-2 respectively, FIG. 6 panel d). Immune-2 antisera reduced the DNA-protein complex produced using murine thymic nuclear extracts significantly, consistent with the relatively equal representation of NF-AT$_c$ and NF-AT$_p$ peptides in the purified protein from bovine thymus.

Example 6

NF-AT$_c$ Dominant Negative Mutant Assayed in Transient Transfection Assays

Figure 7:
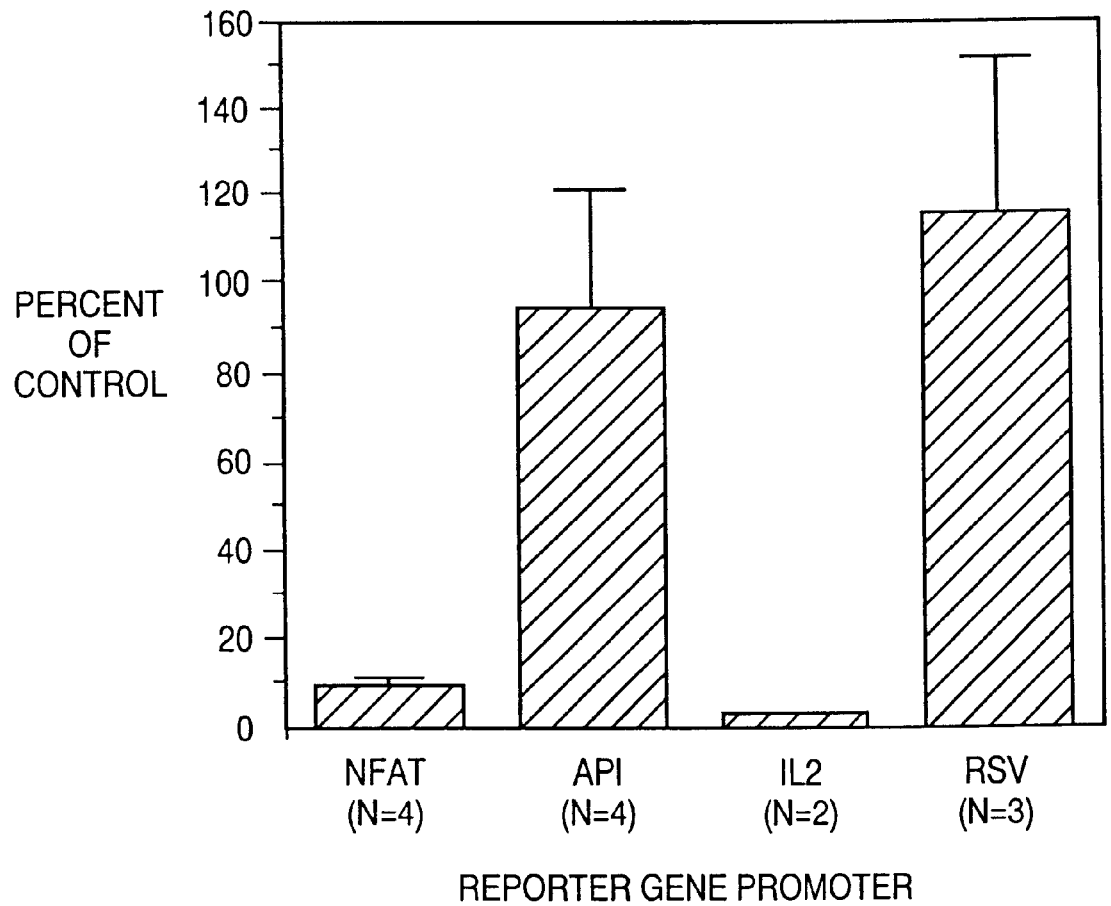
FIG. 7 shows dominant-negative $NF\text{-}AT_c$. Jurkat Tag cells were transfected with vector plasmid (control) or with the dominant negative $NF\text{-}AT_c$ plasmid, plus the indicated secreted alkaline phosphatase reporter plasmid. Transfected cells were transferred to fresh culture medium 24 hours after transfection and secreted alkaline phosphatase activity was measured (Clipstone and Crabtree (1992) *Nature* 357: 695–698) 16 to 24 hours later, after stimulation with 1 uM ionomycin plus 20 ng/ml PMA (NF-AT and IL-2 reporters), 20 ng/ml PMA alone (API reporter) or no stimulation (RSV reporter). Bars indicate, secreted alkaline phosphatase activity from cells transfected with the dominant negative $NF\text{-}AT_c$ as a percentage of the activity from cells transfected in parallel with control plasmid, and represent data obtained from (n) independent transfections. The dominant negative $NF\text{-}AT_c$ consists of a carboxy terminal truncation of the epitope tagged $NF\text{-}AT_c$ expression plasmid extending to the PvuII site at amino acid 463.

A dominant negative NF-AT$_c$, prepared after extensive deletion analysis of the cDNA, indicated that the amino terminal domain would block NF-AT-dependent function without affecting binding. This region of the cDNA is not found in NF-AT$_p$ and hence can be used to assess the contribution of NF-AT$_c$ to the activation of the IL-2 gene. The dominant negative NF-AT$_c$ used consists of a carboxy terminal truncation of the epitope tagged NF-AT$_c$ expression plasmid (suora) extending to the PvuII site at amino acid 463. Transfection of this dominant negative resulted in more than 90% inhibition of IL-2 promoter function as well as transcription directed by the NF-AT site (FIG. 7). This effect was highly specific since transcription directed by the AP-1 site or the RSV promoter and enhancer were relatively unaffected (FIG. 7). These results strongly indicate that NF-AT$_c$ contributes substantially to IL-2 gene expression in T cells.

Dominant-negative NF-AT$_c$ polypeptides or peptidomimetics thereof can be used as pharmaceutical antagonists of NF-AT-mediated activation of T cells. In one variation, such drugs can be used as commercial research reagents for laboratory testing and analysis of T cell activation and the like, among many other uses (e.g., immunosuppressant).

Example 7

Post-Translational Modification of NF-AT$_c$

Figure 8:
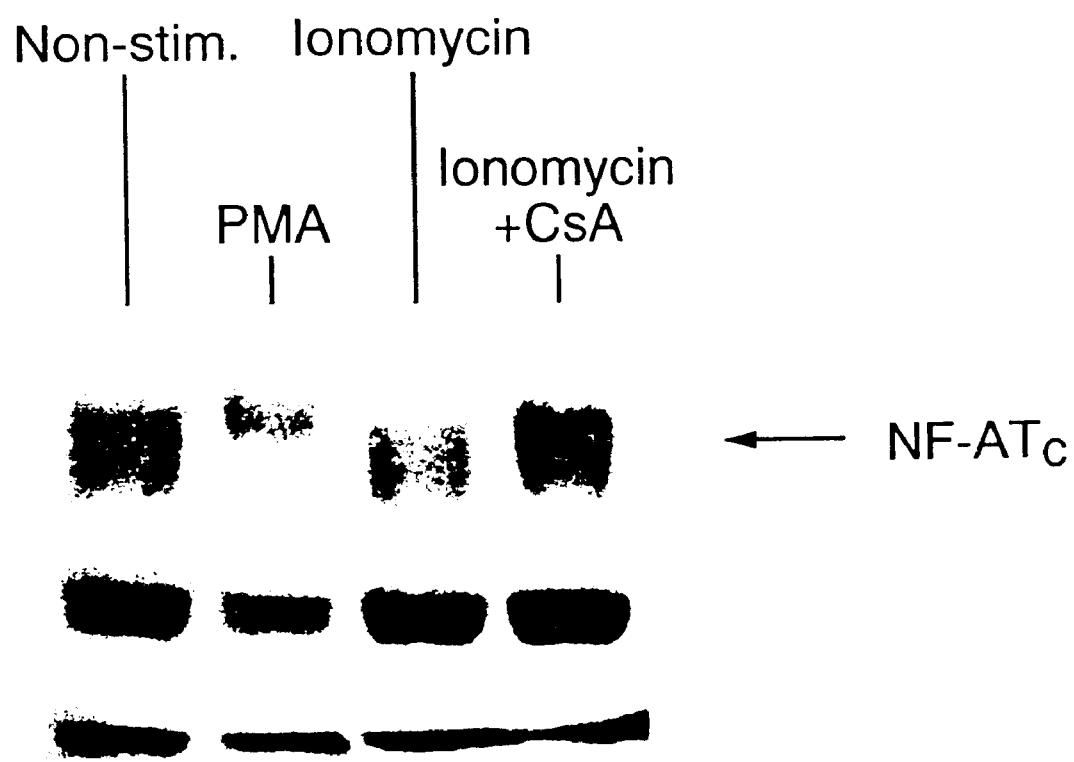
FIG. 8 shows changes in mobility of epitope tagged $NF\text{-}AT_c$ expressed in Jurkat cells. Cells were transfected with $NF\text{-}AT_c$ as in FIG. 2 and stimulated as shown for 2 hrs plus or minus 100 ng/ml CsA. Whole cell lysates were analyzed by western blotting as in FIG. 2.

Post-translational modification of NF-AT$_c$ was investigated in cells treated with agents that activate PKC or increase intracellular $Ca^{++}$. Cells were transfected with NF-AT$_c$ as described in FIG. 2 and stimulated as shown for 2 hrs plus or minus 100 ng/ml CsA. Whole cell lysates were analyzed by western blotting as in FIG. 2. The bulk of NF-AT$_c$ in cells treated with ionomycin migrates faster than that in non-treated cells and this mobility shift is inhibited by CsA (FIG. 8, lanes 1, 3–4). This is consistent with a dephosphorylation event, possibly by direct action of calcineurin (Clipstone and Crabtree (1992) Nature 357: 695–697), however, any of a large number of processes could produce the observed mobility changes. There is evidence that NF-AT$_p$ is a substrate for calcineurin, however, the mobility shifts produced by phosphatase treatment of NF-AT$_p$ or NF-AT$_c$ are far greater than those observed in FIG. 8. These observations indicate that NF-AT$_c$ is not a direct substrate of calcineurin. PMA treatment produces a slower migrating NF-AT$_c$ (FIG. 8, lane 2); therefore, PKC-activated pathways likely contribute to NF-AT activity by modification of NF-AT$_c$ in addition to activation of the nuclear component.

Although the present invention has been described in some detail by way of illustration for purposes of clarity of understanding, it will be apparent that certain changes and modifications may be practiced within the scope of the claims.

What is claimed is:

1. An isolated polynucleotide primer or probe comprising at least 20 nucleotides which hybridizes specifically to a nucleotide sequence set forth in SEQ ID NO: 45, or to the complement thereof, under stringency conditions of 5×SSC at 42° C.

2. The isolated polynucleotide primer or probe of claim 1, which hybridizes specifically to a nucleotide sequence of SEQ ID NO: 45 which encodes the Rel Similarity Region or to the complement thereof.

3. The isolated polynucleotide primer or probe of claim 1, which hybridizes specifically to a nucleotide sequence of SEQ ID NO: 45 in a region located outside of the sequence encoding the Rel Similarity Region, or to the complement thereof.

4. The isolated polynucleotide primer or probe of claim 1 which comprises at least 20 consecutive nucleotides of SEQ ID NO: 45, or the complement thereof.

5. The isolated polynucleotide primer or probe of claim 1, which hybridizes specifically to a nucleotide sequence set forth in SEQ ID NO: 45, or to the complement thereof, under stringency conditions of 5×SSC at 70° C.

6. The isolated polynucleotide primer or probe of claim 1, which is selected from the group consisting of any one of SEQ ID NO: 1–22 or the complement thereof.

7. The isolated polynucleotide primer or probe of claim 1, further comprising a label.

8. The isolated polynucleotide primer or probe of claim 1, which hybridizes specifically to the nucleotide sequence set forth in SEQ ID NO: 45, or to the complement thereof, under stringency conditions of 5×SSC at 42° C. followed by washing in 3×SSC at 50° C.

9. The isolated polynucleotide primer or probe of claim 4 which comprises at least 25 consecutive nucleotides of SEQ ID NO: 45, or the complement thereof.

10. The isolated polynucleotide primer or probe of claim 9 which comprises at least 50 nucleotides of SEQ ID NO: 45, or the complement thereof.

11. The isolated polynucleotide primer or probe of claim 10 which comprises at least 100 nucleotides of SEQ ID NO: 45, or the complement thereof.

12. An isolated polynucleotide primer or probe comprising at least 20 nucleotides, which hybridizes specifically to a polynucleotide encoding an NF-AT polypeptide having the amino acid sequence set forth in SEQ ID NO: 38, or to the complement thereof, under stringency conditions of 5×SSC at 42° C.

13. A method for determining the presence and/or amount of an NF-AT polynucleotide encoding a cytoplasmic component of an NP-AT complex in a cell, comprising
    (i) contacting a cell, or polynucleotides thereof, with a polynucleotide primer or probe comprising at least 20 nucleotides which hybridizes specifically to a nucleotide sequence set forth in SEQ ID NO: 45, or to the complement thereof, under stringency conditions of 5×SSC at 42° C, and
    (ii) determining, by detection of the polynucleotide primer or probe, the presence and/or amount of the NF-AT polynucleotide in the cell, or polynucleotides thereof.

14. The method of claim 13, wherein the polynucleotide primer or probe hybridizes specifically to a nucleotide sequence of SEQ ID NO: 45 which encodes the Rel Similarity Region, or to the complement thereof.

15. The method of claim 13, wherein the polynucleotide primer or probe hybridizes specifically to a nucleotide sequence of SEQ ID NO: 45 in a region located outside of the sequence encoding the Rel Similarity Region, or to the complement thereof.

16. The method of claim 13, wherein the polynucleotide primer or probe comprises at least 20 consecutive nucleotides of SEQ ID NO: 45, or the complement thereof.

17. The method of claim 13, wherein the polynucleotide primer or probe comprises at least 25 consecutive nucleotides of SEQ ID NO: 45, or the complement thereof.

18. The method of claim 13, wherein the polynucleotide primer or probe hybridizes specifically to a nucleotide sequence set forth in SEQ ID NO: 45, or to the complement thereof, under stringency conditions of 5×SSC at 70° C.

19. A method for determining whether a subject has an immune hyperfunction or hypofunction, comprising
    (i) obtaining immune cells from a subject; and
    (ii) detecting the level of NF-AT mRNA in the immune cells of a subject according to the method of claim 13, wherein the presence of a higher or lower NF-AT mRNA level in the immune cells of the subject relative to that in immune cells in a subject which has a normal immune status, indicates that the subject has an immune hyperfunction or hypofunction, respectively.

20. A method for determining whether a transplant rejection is occurring in a subject, comprising
    (i) identifying a subject having a transplant; and
    (ii) detecting the level of NF-AT mRNA in an immune cell of a subject according to the method of claim 13, wherein the presence of a higher NF-AT mRNA level in the immune cell of the subject relative to that in an immune cell in a subject which has a normal immune status, indicates that a transplant rejection is occurring in the subject.

21. A method for determining whether a subject has, or is likely to develop, an autoimmune disease, comprising
    (i) identifying a subject who is likely to have an autoimmune disease; and
    (ii) detecting the level of NF-AT mRNA in an immune cell of a subject according to the method of claim 13, wherein the presence of a higher NF-AT mRNA level in the immune cell of the subject relative to that in an immune cell in a subject which has a normal immune status, indicates that the subject has, or is likely to develop, an autoimmune disease.

22. A method for determining whether a subject has, or is likely to develop, an immune deficiency, comprising
    (i) identifying a subject who is likely to have an immune deficiency; and
    (ii) detecting the level of NF-AT mRNA in an immune cell of a subject according to the method of claim 13, wherein the presence of a lower NF-AT mRNA level in the immune cell of the subject relative to that in an immune cell in a subject which has a normal immune status, indicates that the subject has, or is likely to develop, an immune deficiency.

23. The method of claim 13, wherein the primer or probe hybridizes specifically to the nucleotide sequence set forth in SEQ ID NO: 45, or to the complement thereof, under stringency conditions of 5×SSC at 42° C. followed by washing in 3×SSC at 50° C.

24. The method of claim 17, wherein the primer or probe comprises at least 50 nucleotides of SEQ ID NO: 45, or the complement thereof.

25. The method of claim 17, wherein the primer or probe comprises at least 100 nucleotides of SEQ ID NO: 45, or the complement thereof.

26. The method of claim 19, wherein the immune cells are T lymphocytes.

27. A method for determining the presence and/or amount of an NF-AT polynucleotide encoding a cytoplasmic component of an NF-AT complex in a cell, comprising
  (i) contacting a cell, or polynucleotides thereof, with a polynucleotide primer or probe comprising at least 20 nucleotides which hybridizes specifically to a polynucleotide encoding an NF-AT polypeptide having the amino acid sequence set forth in SEQ ID NO: 38, or to the complement thereof, under stringency conditions of 5×SSC at 42° C., and
  (ii) determining, by detection of the polynucleotide primer or probe, the presence and/or amount of the NF-AT polynucleotide in the cell, or polynucleotides thereof.

* * * * *